(12) United States Patent
Shlomi et al.

(10) Patent No.: US 11,826,353 B2
(45) Date of Patent: Nov. 28, 2023

(54) METHOD AND SYSTEM FOR TREATING CANCER

(71) Applicant: TECHNION RESEARCH AND DEVELOPMENT FOUNDATION LIMITED, Haifa (IL)

(72) Inventors: Tomer Shlomi, Kfar Hes (IL); Won Dong Lee, Seoul (KR)

(73) Assignee: TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 681 days.

(21) Appl. No.: 17/025,269

(22) Filed: Sep. 18, 2020

(65) Prior Publication Data

US 2021/0077462 A1     Mar. 18, 2021

Related U.S. Application Data

(60) Provisional application No. 62/901,920, filed on Sep. 18, 2019.

(51) Int. Cl.
*A61K 31/4162* (2006.01)
*A61P 35/00* (2006.01)
*G01N 33/574* (2006.01)

(52) U.S. Cl.
CPC .......... *A61K 31/4162* (2013.01); *A61P 35/00* (2018.01); *G01N 33/57484* (2013.01)

(58) Field of Classification Search
CPC .. A61K 31/4162; A61P 35/00; G01N 33/5784
USPC ........................................................ 514/406
See application file for complete search history.

(56) References Cited

FOREIGN PATENT DOCUMENTS

WO         2016/145252 A1      9/2016

OTHER PUBLICATIONS

Antoniewicz, et al., Determination of confidence intervals of metabolic fluxes estimated from stable isotope measurements, Metabolic Engineering, 2006, pp. 324-337, vol. 8.
Antoniewicz, et al., Elementary metabolite units (EMU): A novel framework for modeling isotopic distributions, Metabolic Engineering, 2007, pp. 68-86, vol. 9.
Bennett, et al., Absolute quantitation of intracellular metabolite concentrations by an isotope ratio-based approach; Nature Protocols, 2008, pp. 1299-1311, vol. 3, No. 8.
Chen, et al., An LC-MS chemical derivatization method for the measurement of five different one-carbon states of cellular tetrahydrofolate, Anal Bioanal Chem, 2017, pp. 1-10.
Ducker, et al., Reversal of Cytosolic One-Carbon Flux Compensates for Loss of the Mitochondrial Folate Pathway, Cell Metabolism, 2016, pp. 1140-1153, vol. 23.
Ducker, et al., One-Carbon Metabolism in Health and Disease, Cell Metabolism, Jan. 2017, pp. , vol. 25.
Ducker, et al., Human SHMT inhibitors reveal defective glycine import as a targetable metabolic vulnerability of diffuse large B-cell lymphoma, PNAS Early Edition, 2017, pp. 1-6.
Fan, et al., Fatty Acid Labeling from Glutamine in Hypoxia Can Be Explained by Isotope Exchange without Net Reductive Isocitrate Dehydrogenase (IDH) Flux, The Journal of Biological Chemistry, Oct. 2013, pp. 31363-31369, vol. 288, No. 43.
Fan, et al., Glutamine-driven oxidative phosphorylation is a major ATP source in transformed mammalian cells in both normoxia and hypoxia, Molecular Systems Biology, 2013, pp. 1-11, vol. 9, article No. 712.
Fan, et al., Quantitative flux analysis reveals folate-dependent NADPH production, Nature, 2014, pp. 1-18, vol. 000.
Fazili, et al., Influence of 5,10-Methylenetetrahydrofolate Reductase Polymorphism on Whole-Blood Folate Concentrations Measured by LC-MS/MS, Microbiologic Assay, and Bio-Rad Radioassay, Clinical Chemistry, 2008, pp. 197-201, vol. 54:1.
Gravel, et al., Serine Deprivation Enhances Anti-neoplastic Activity of Biguanides, Cancer Research, 2014, pp. 1-36.
Hou, et al., Biology of the Major Facilitative Folate Transporters SLC19A1 and SLC46A1, Current Topics in Membranes, 2014, pp. 175-204, vol. 73.
Jain, et al., Metabolite Profiling Identifies a Key Role for Glycine in Rapid Cancer Cell Proliferation, Science, May 2012, pp. 1040-1044, vol. 336.
Klijn, et al., A comprehensive transcriptional portrait of human cancer cell lines, Nature Biotechnology, Advance Online Publication, 2014, pp. 1-10.
Lewis, et al., Tracing Compartmentalized NADPH Metabolism in the Cytosol and Mitochondria of Mammalian Cells, Molecular Cell, Jul. 2014, pp. 1-11, vol. 55.
Maddocks, et al., Serine starvation induces stress and p53-dependent metabolic remodelling in cancer cells, Nature, 2012, pp. 1-7, vol. 000.
Marani, et al., A pyrazolopyran derivative preferentially inhibits the activity of human cytosolic serine hydroxymethyltransferase and induces cell death in lung cancer cells, Oncotarget, 2015, pp. 4570-4583.
Meiser, et al., Serine one-carbon catabolismwith formate overflow, Sci. Adv., Oct. 2016, pp. 1-0, vol. 2:e1601273.
Meiser, et al., Increased formate overflow is a hallmark of oxidative cancer, Nature Communication, 2018, pp. 1-12, vol. 9:1368.
Melamud, et al., Metabolomic Analysis and Visualization Engine for LC-MS Data, Anal. Chem., 2010, pp. 9818-9826, vol. 82.
Millard, et al., IsoCor: correcting MS data in isotope labeling experiments, Bioinformatics Applications Note, 2012, pp. 1294-1296, vol. 28, No. 9.
Newman, et al., One-carbon metabolism in cancer, British Journal of Cancer, 2017, pp. 1499-1504, vol. 116.
Nilsson, et al., Metabolic enzyme expression highlights a key role for MTHFD2 and the mitochondrial folate pathway in cancer, Nature Communications, 2014, pp. 1-10, vol. 5:3128.

(Continued)

*Primary Examiner* — Yevgeny Valenrod
(74) *Attorney, Agent, or Firm* — BROWDY AND NEIMARK, PLLC

(57) ABSTRACT

The invention provides a method for treating cancer in which a level of reduced folate carrier (RFC) or folylpolyglutamate synthetase (FPGS) in cancer cells of the biopsy is determined. If the level of RFC or FPGS in the cancer cells is below a threshold value, the cancer is treated with an inhibitor of serine-hydroxymethyl-transferase (SHMT)1. If the level of RFC or FPGS in the cancer cells is above the threshold value, the cancer is treated with an inhibitor of SHMT2.

11 Claims, 12 Drawing Sheets

Specification includes a Sequence Listing.

(56) References Cited

OTHER PUBLICATIONS

Pacold, et al., A PHGDH inhibitor reveals coordination of serine synthesis and one-carbon unit fate, Nature Chemical Biology, Advance Online Publication, Apr. 2016, pp. 1-10.
Rothem, et al., Resistance to multiple novel antifolates is mediated via defective drug transport resulting from clustered mutations in the reduced folate carrier gene in human leukaemia cell lines, Biochem J., 2002, pp. 741-750, vol. 367.
Tibbetts, et al., Compartmentalization of Mammalian Folate-Mediated One-Carbon Metabolism, Annu. Rev. Nutr., 2010, pp. 57-81, vol. 30.
Otto Warburg, On the Origin of Cancer Cells, Science, Feb. 1956, pp. 309-314, vol. 123, No. 3191.
Wishart, et al., HMDB 4.0; the human metabolome database for 2018, Nucleic Acids Research, 2018, pp. D608-D617, vol. 46.

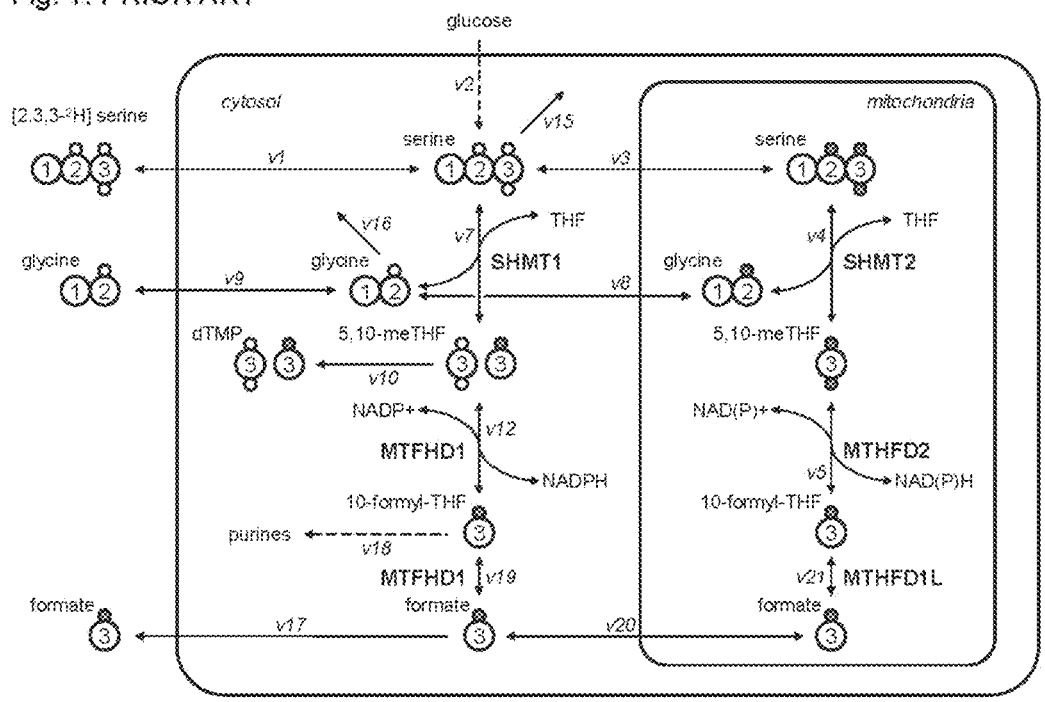
Fig. 1: PRIOR ART

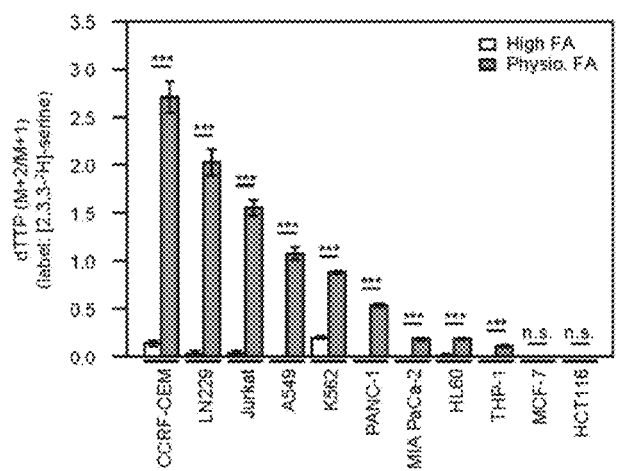
Fig. 2A
Fig. 2C
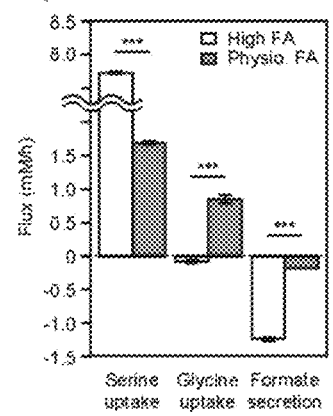
Fig. 2B
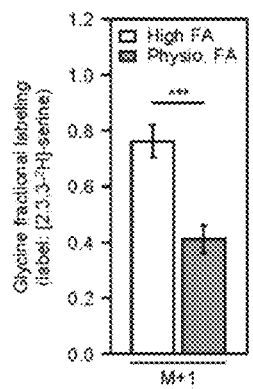
Fig. 2D
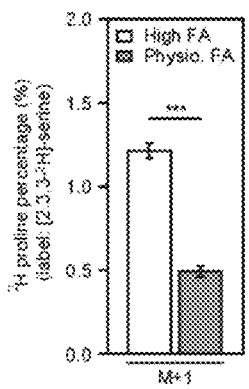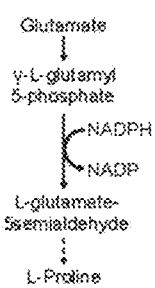
Fig. 2E
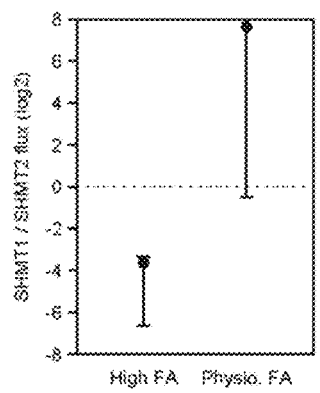

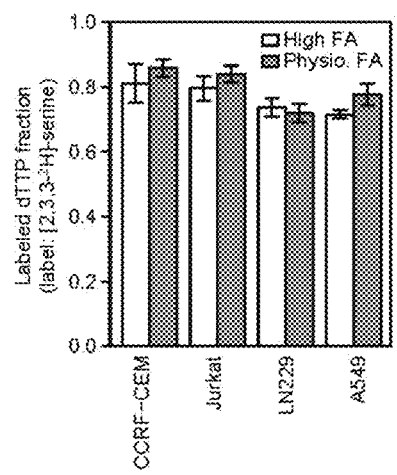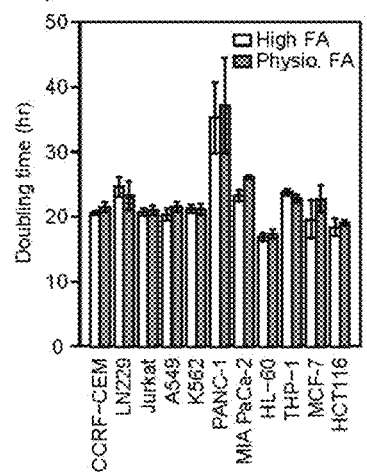

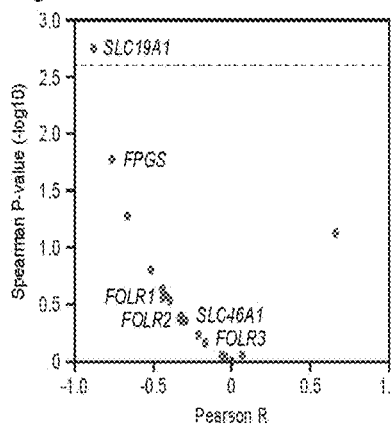
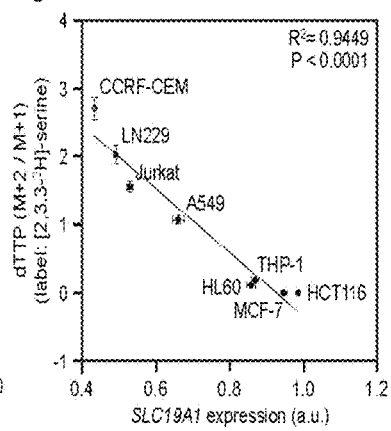
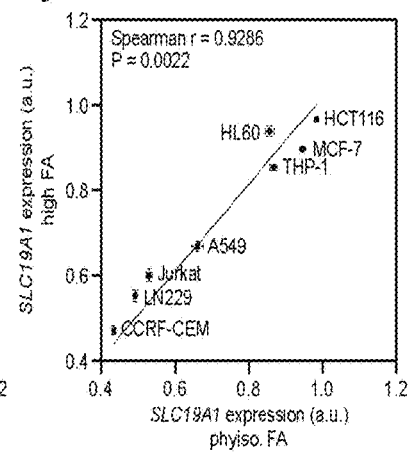
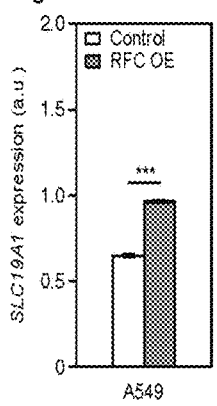
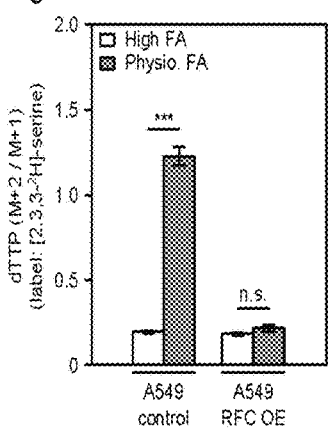
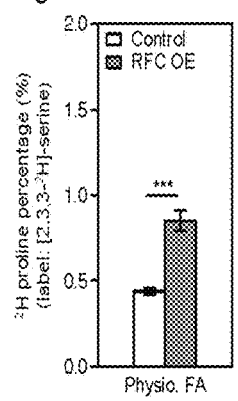
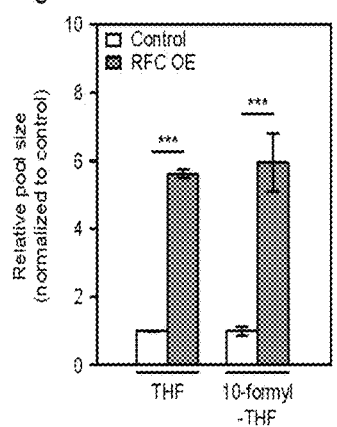
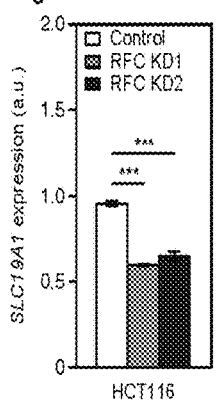
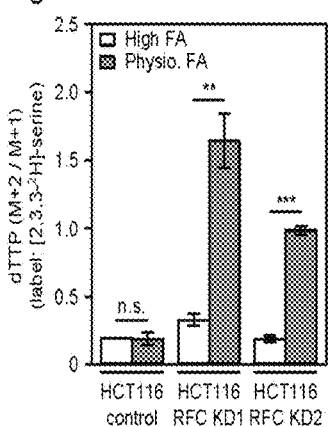
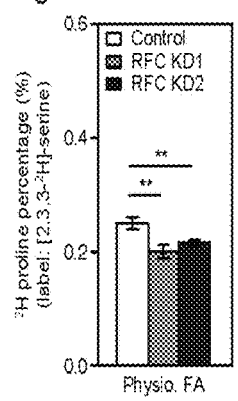
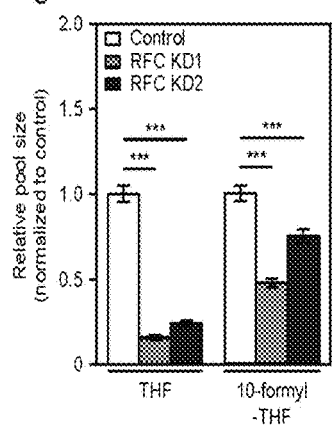

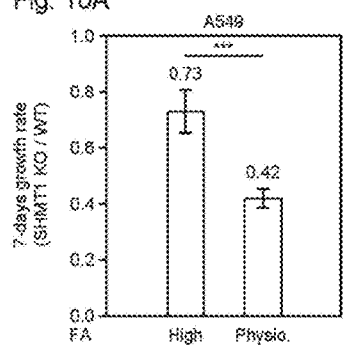
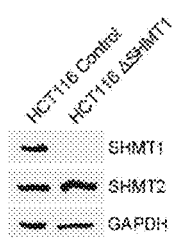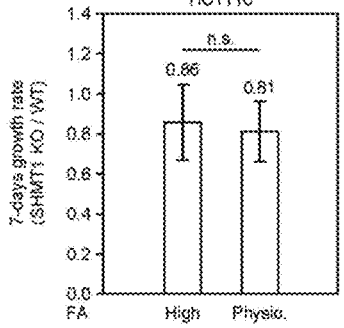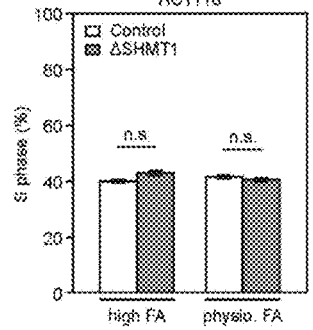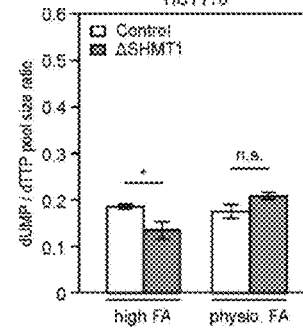

METHOD AND SYSTEM FOR TREATING CANCER

The present application claims the benefit under 35 U.S.C. 119(e) of U.S. Provisional Application 62/901,920 filed on Sep. 18, 2019 the disclosure of which is incorporated herein by reference.

The Sequence Listing in ASCII text file format of 2,090 bytes in size, created on Oct. 15, 2020, with the file name "2020-11-19SequenceListing_SHLOMI1," filed in the U.S. Patent and Trademark Office on even date herewith, is hereby incorporated herein by reference.

FIELD OF THE INVENTION

The present invention relates to methods and systems for diagnosing and treating cancer.

BACKGROUND OF THE INVENTION

The following publications are considered as being relevant for an understanding of the background of the invention:

1. Antoniewicz, M. R., Kelleher, J. K., and Stephanopoulos, G. (2006). Determination of confidence intervals of metabolic fluxes estimated from stable isotope measurements. 8, 324-337.
2. Antoniewicz, M. R., Kelleher, J. K., and Stephanopoulos, G. (2007). Elementary metabolite units (EMU): A novel framework for modeling isotopic distributions. Metab. Eng. 9, 68-86.
3. Bennett. B. D. Yuan, J., Kimball, E. H., and Rabinowitz, J. D. (2008). Absolute quantitation of intracellular metabolite concentrations by an isotope ratio-based approach. Nat. Protoc. 3, 1299-1311.
4. Chen, L., Ducker, G. S., Lu, W., Teng, X., and Rabinowitz, J. D. (2017). An LC-MS chemical derivatization method for the measurement of five different one-carbon states of cellular tetrahydrofolate. Anal. Bioanal. Chem. 409, 5955-5964.
5. Ducker, G. S., and Rabinowitz, J. D. (2017). One-Carbon Metabolism in Health and Disease. Cell Metab. 25, 27-42.
6. Ducker, G. S., Chen, L., Morscher, R. J., Ghergurovich, J. M., et al. (2016). Reversal of Cytosolic One-Carbon Flux Compensates for Loss of the Mitochondrial Folate Pathway Article Reversal of Cytosolic One-Carbon Flux Compensates for Loss of the Mitochondrial Folate Pathway. Cell Metab. 23, 1140-1153.
7. Ducker. G. S., Ghergurovich. J. M., Mainolfi, N., Suri, V., Jeong, S. K., Li, S. H. J., Friedman, A., Manfredi, M. G., Gitai, Z., Kim, H., et al. (2017). Human SHMT inhibitors reveal defective glycine import as a targetable metabolic vulnerability of diffuse large B-cell lymphoma. Proc. Natl. Acad. Sci. U.S.A 114, 11404-11409.
8. Fan, J., Kamphorst, J. J., Rabinowitz, J. D., and Shlomi, T. (2013a). Fatty acid labeling from glutamine in hypoxia can be explained by isotope exchange without net reductive isocitrate dehydrogenase (IDH) flux. J. Biol 288(43), 31363-31369.
9. Fan, J., Kamphorst, J. J., Mathew, R., Chung, M. K., White, E., Shlomi, T., and Rabinowitz, J. D. (2013b). Glutamine-driven oxidative phosphorylation is a major ATP source in transformed mammalian cells in both normoxia and hypoxia. Mol. Syst. Biol. 9, 217.
10. Fan, J., Ye, J., Kamphorst, J. J., Shlomi, T., Thompson, C. B., and Rabinowitz, J. D. (2014). Quantitative flux analysis reveals folate-dependent NADPH production. Nature 510, 298-302.
11. Fazili, Z., Pfeiffer, C. M., Zhang, M., Jain, R. B., Koontz, D., and Scott, J. M. (2008). Influence of 5,10-methylenetetrahydrofolate reductase polymorphism on whole-blood folate concentrations measured by LC-MS/MS, microbiologic assay, and bio-rad radioassay. Clin. Chem. 54, 197-201.
12. Gravel, S.-P., Hulea, L., Toban, N., Birman, E., Blouin, M.-J., Zakikhani, M., Zhao, Y., Topisirovic. I., St-Pierre, J., and Pollak, M. (2014). Serine Deprivation Enhances Antineoplastic Activity of Biguanides. Cancer Res. 74, 7521-7533.
13. Hou. Z., and Matherly, L. H. (2014). Biology of the major facilitative folate transporters SLC19A1 and SLC46A1. In Current Topics in Membranes, p.
14. Jain, M., Nilsson, R., Sharma. S., Madhusudhan, N., Kitami, T., Souza, A. L., Kafri, R., Kirschner, M. W., Clish, C. B., and Mootha, V. K. (2012). Metabolite profiling identifies a key role for glycine in rapid cancer cell proliferation. Science (80-.). 336, 1040-1044.
15. Klijn, C., Durinck, S., Stawiski, E. W., Haverty, P. M., Jiang, Z., Liu, H., Degenhardt, J., Mayba. O., Gnad, F., Liu, J., et al. (2015). A comprehensive transcriptional portrait of human cancer cell lines. Nat. Biotechnol. 33, 306-312.
16. Lewis, C. A., Parker, S. J., Fiske, B. P., McCloskey, D., Gui, D. Y., Green, C. R., Vokes, N. I., Feist, A. M., Vander Heiden, M. G., and Metallo, C. M. (2014). Tracing Compartmentalized NADPH Metabolism in the Cytosol and Mitochondria of Mammalian Cells. *Mol. Cell* 55, 253-263.
17. Maddocks, O. D. K., Berkers, C. R., Mason, S. M., Zheng, L., Blyth, K., Gottlieb, E., and Vousden, K. H. (2013). Serine starvation induces stress and p53-dependent metabolic remodelling in cancer cells. Nature 493, 542-546.
18. Marani M, Paone A., Fiascarelli A., Macone A., Gargano M., Rinaldo S., Giardina G., Pontecorvi V., Koes D., McDermott L., Yang T., Paiardini A., Contestabile R., and Cutruzzolá F. (2016) A pyrazolopyran derivative preferentially inhibits the activity of human cytosolic serine hydroxymethyltransferase and induces cell death in lung cancer cells. Oncotarget 7(4), 4570-4583
19. Meiser, J., Tumanov, S., Maddocks, O., Labuschagne, C. F., Athineos, D., Van Den Broek, N., Mackay, G. M., Gottlieb, E., Blyth, K., Vousden, K., et al. (2016). Serine one-carbon catabolism with formate overflow. Sci. Adv. 2.
20. Meiser. J., Schuster, A., Pietzke, M., Voorde. J. Vande, Athineos, D., Oizel. K., Burgos-Barragan. G., Wit, N., Dhayade, S., Morton, J. P., et al. (2018). Increased formate overflow is a hallmark of oxidative cancer. Nat. Commun. 9.
21. Melamud, E., Vastag. L., and Rabinowitz. J. D. (2010). Metabolomic analysis and visualization engine for LC-MS data. Anal. Chem. 82, 9818-9826.
22. Millard, P., Letisse, F., Sokol, S., and Portais, J. C. (2012). IsoCor: Correcting MS data in isotope labeling experiments. Bioinformatics 28, 1294-1296.
23. Newman, A. C., and Maddocks, O. D. K. (2017). One-carbon metabolism in cancer. Br. J. Cancer 116, 1499-1504.
24. Nilsson, R., Jain, M., Madhusudhan, N., Sheppard, N. G., Strittmatter, L., Kampf, C., Huang, J., Asplund, A., and Mootha. V. K. (2014). Metabolic enzyme expression highlights a key role for MTHFD2 and the mitochondrial folate pathway in cancer. Nat. Commun. 5.
25. Pacold, M. E., Brimacombe, K. R., Chan, S. H., Rohde, J. M., Lewis, C. A., Swier, L. J. Y. M., Possemato, R., Chen, W. W., Sullivan, L. B., Fiske, B. P., et al. (2016). A PHGDH inhibitor reveals coordination of serine synthesis and one-carbon unit fate. Nat. Chem. Biol. 12, 452-458.

26. Rothem, L., Ifergan, I., Kaufman, Y., Priest, D. G., Jansen, G., and Assaraf, Y. G. (2002). Resistance to multiple novel antifolates is mediated via defective drug transport resulting from clustered mutations in the reduced folate carrier gene in human leukaemia cell lines. Biochem. J. 367, 741-750.
27. Tibbetts, A. S., and Appling, D. R. (2010). Compartmentalization of Mammalian Folate-Mediated One-Carbon Metabolism. Annu. Rev. Nutr. 30, 57-81.
28. Warburg, O. (1956). On the Origin of Cancer Cells. Science (80-.). 123, 309-314.
29. Wishart, D. S., Feunang, Y. D., Marcu, A., Guo, A. C., Liang, K., Vázquez-Fresno, R., Sajed, T., Johnson, D., Li, C., Karu, N., et al. (2018). HMDB 4.0: The human metabolome database for 2018. Nucleic Acids Res. 46, D608-D617.
30. International Patent Publication WO2016145252 of Rabinowitz et al.

Enzymes of the folate cycle are among the most consistently overexpressed proteins in cancer. Folate metabolism supplies one-carbon (1C) units for biosynthesis and methylation. The folate cycle mediates the transfer of 1C units to support biosynthesis of DNA and RNA as well shuttling of 1C units to the methionine cycle to support DNA and protein methylation (Locasale, 2013). Tetrahydrofolate (THF), a reduced form of dietary folic acid (vitamin B9), is the carrier of the 1C moieties, primarily derived from amino acid catabolism.

A folate cycle is present in the mitochondria and in the cytosol, with distinct isozymes catalyzing similar reactions in the two subcellular compartments (Tibbetts and Appling, 2010b). FIG. 1 shows a compartmentalized view of the folate cycle showing the use of [2,3,3-$^2$H]-serine as a tracer for distinguishing between cytosolic and mitochondrial 1C flux into pyrimidines. Thymidine with two deuterium atoms (M+2) is synthesized via the cytosolic folate cycle through the enzyme serine-hydroxymethyltransferase 1 (SHMT1). Thymidine with one deuterium (M+1) is synthesized via mitochondrial SHMT2. Mitochondrial serine-derived methylene-THF is oxidized to formate, transported to the cytosol, incorporated into THF, and eventually reduced back to 5,10-methylene-THF, synthesizing dTTP.

The importance of 1C metabolism in cancer was discovered about 60 years ago when it was found that the folate antagonist aminopterin produced remission in children with acute lymphoblastic leukemia, starting the era of chemotherapy (Chabner and Roberts, 2005). Antifolates, such as methotrexate and pemetrexed, which directly interfere with 1C flow towards biosynthesis of deoxynucleotides are still widely used in the treatment of various human hematologic malignancies and solid tumors (Ducker and Rabinowitz, 2017). Recently, frequent tumor-specific alterations in the expression of 1C metabolic enzymes have been found. This has led to several important discoveries of new components of this system (Gu et al., 2017: Kory et al., 2018: Zheng et al., 2018), promiscuous activity of 1C enzymes (Morscher et al., 2018), dependence on nutrient availability (Maddocks et al., 2013), and the development of drugs that inhibit 1C enzymes (Ducker et al., 2017).

Recent studies highlighted an important role of the mitochondrial folate cycle in tumors. This was supported by the finding of mitochondrial methylenetetrahydrofolate dehydrogenase (MTHFD2) being the most frequently upregulated metabolic gene across cancers (Nilsson et al., 2014). Isotope tracing studies suggested that the mitochondrial folate cycle is the sole contributor of 1C units for biosynthesis in cancer, with mitochondrially derived 1C units shuttled to cytosol in the form of formate (Ducker et al., 2016; Lewis et al., 2014). Serine-derived 1C flux in mitochondria was reported to far exceed the anabolic requirements of cancer cells, leading to formate secretion from cells (Meiser et al., 2016, 2018). This has led to the conclusion that mitochondrial serine catabolism is the predominate contributor of folate-mediated 1C units in proliferating cancer cells.

Inhibition of the mitochondrial SHMT2 has been tested for a potential anti-cancer effect, but it was found that cells readily compensate for the inhibition of SHMT2 by switching on the cytosolic pathway (Ducker et al., 2016). This has motivated the development of drugs that target both SHMT1 and SHMT2 (referred to herein as "dual SHMT1/2 inhibitors") (Ducker et al., 2017). However, an inhibitor of both SHMT1 and SHMT2 is expected to have a detrimental effect on normal cells, and as such, would have limited utility in the in vivo treatment of cancer.

The conclusion that mitochondrial serine catabolism is the predominate contributor of folate-mediated 1C units in proliferating cancer cells is based on experimental results performed in standard tissue culture conditions, in which the total folate concentration is an order of magnitude higher than that in human serum (150-450 nM in serum (Fazili et al., 2008: Wishart et al., 2018) versus 2.2 µM and 9 µM in RPMI and DMEM, respectively). However, it is known that substrate availability in the tumor microenvironment plays an important role in tumor 1C metabolism. For example, restriction of dietary serine and glycine can reduce tumor growth in vivo (Gravel et al., 2014; Maddocks et al., 2013), and serum folate levels affect cancer risk and tumor progression (Ashkavand et al., 2017: Kim, 2007).

Pyrazolopyran compound inhibitors of SHMT that are more effective against SHMT1 than SHMT2 have been described (Marani et al., 2016; Drucker et al., 2017) and International Patent Publication WO2016145252 of Rabinowitz et al. Marani et al showed depletion of SHMT1 in lung cancer cell lines causes cell cycle arrest and ultimately apoptosis.

SUMMARY OF THE INVENTION

The present invention is based on the novel and unexpected discovery of a number of cancers in which, under physiological folate levels in the cell environment, cytosolic 1C flux, and not mitochondrial 1C flux, is the predominant contributor of folate-mediated 1C. The invention is further based on the novel and unexpected observation that the reliance on cytosolic 1C flux in these cells may be due to reduced expression of one or both of the gene SLC19A1 which encodes for the reduced folate carrier (RFC) and the gene encoding for folylpolyglutamate synthetase (FPGS). RFC transports folate into the cell while transporting an anion out of the cell. Without wishing to be bound by a particular theory, it is believed that the reduced expression of RFC or FPGS at physiological levels of extracellular folate leads in these cells to impaired maintenance of an adequate level of intracellular folate. The inventors have found that, in cells with low RFC expression, silencing SHMT1, with or without impairing SHMT2, impairs pyrimidine biosynthesis and tumor growth.

Thus, in one of its aspects, the present invention provides a method for treating cancer in an individual comprising:
a. obtaining a biopsy of the cancer;
b. measuring one or both of: (i) a level reduced folate carrier (RFC) in cancer cells of the biopsy, and (ii) a level folylpolyglutamate synthetase (FPGS) in cancer cells of the biopsy;
c. determining one or both of: (i) whether the level of RFC in the cancer cells is above or below a first predetermined threshold value, and (ii) whether the level of FPGS folylpolyglutamate synthetase (FPGS) in the cancer cells is above or below a second predetermined threshold value;
d. if the level of RFC in the cancer cells is below the first predetermined threshold, treating the individual with an inhibitor of serine-hydroxymethyltransferase (SHMT)1 in a pharmaceutically acceptable carrier;
e. if the level of FPGS in the cancer cells is below the second predetermined threshold, treating the individual with an inhibitor of serine-hydroxymethyltransferase (SHMT)1 in a pharmaceutically acceptable carrier; and or FPGS
f. if the level of RFC in the cancer cells is above the first predetermined threshold, treating the individual with an inhibitor of serine-SHMT2 in a pharmaceutically acceptable carrier, and
g. if the level of FPGS in the cancer cells is above the second predetermined threshold, treating the individual with an inhibitor of serine-SHMT2 in a pharmaceutically acceptable carrier The RFC level may be determined directly from the amount of RFC in the cells, or from the expression level of the SLC19A1 gene. If the RFC level is determined from the expression level of the SLC19A1 gene, the expression level of the SLC19A1 gene in the cancer cells may be measured, for example, in units of "reads per kilobase of transcript per million mapped reads" (RPKM). Other units of gene expression level may also be used such as "fragments per kilobase of transcript" (FPKM) and "transcripts per kilobase million" (TPM).

For example, when units of gene expression of RPKM are used, in an embodiment of the invention, a threshold value of 4 RPKM may be used. In another embodiment, a threshold value of 3 RPKM may be used. In yet another embodiment, a threshold value of 2 RPKM may be used.

The method of the invention may be carried out with any SHMT inhibitor. For example, the method of the invention may be carried out using any one of the SHMT inhibitors disclosed in (Marani et al., 2016; Drucker et al., 2017, and in International Patent Publication WO2016145252. These publications also disclose inhibitors of SHMT having a higher specificity for SHMT1 over SHMT2.

For example, the method may be carried out using an SHMT1 inhibitor that is a pyrazolopyran derivative. The pyrazolopyran derivative may be, for example, ((4R)-6-amino-4-ethyl-4-(3, 5-chlorophenyl)-1H-pyrano[2,3-c]pyrazole-5-carbonitrile), described in Marani et al (2016). As another example, the pyrazolopyran derivative may have an isopropyl group at the chiral four-carbon of the pyrano ring or an aromatic substitution at the chiral four-carbon of the pyrano ring, as disclosed in Drucker et al (2017). As yet another example, the SHMT inhibitor may be an enantiomer of the compound referred to as HK-16 in International Patent Publication WO2016145252.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 shows a compartmentalized view of the folate cycle and [2,3,3-$^2$H]-serine tracer for inferring cytosolic versus mitochondrial 1C flux into pyrimidines;

FIG. 2A shows measured dTTP M+2/M+1, representing the cytosolic over the mitochondrial 1C flux, when feeding various cell lines with [2,3,3-$^2$H]-serine in high and physiological media folate levels (n.s. not significant. ***$P<0.001$ by two-sample t-test. Data are mean±SD, n=3 independent biological replicates);

FIG. 2B shows uptake/secretion rates of serine, glycine, and formate of CCRF-CEM in high and physiological media folate levels (***$P<0.001$ by two-sample t-test. Data are mean±SD, n=3 independent biological replicates);

FIG. 2C shows fractional labeling of intracellular glycine when feeding CCRF-CEM with [2,3,3-$^2$H]-serine in high and physiological media folate levels (***$P<0.001$ by two-sample t-test. Data are mean±SD, n=3 independent biological replicates);

FIG. 2D shows percent labeling of intracellular proline when feeding CCRF-CEM with [2,3,3-$^2$H]-serine in high and physiological media folate levels (***$P<0.001$ by two-sample t-test. Data are mean±SD, n=3 independent biological replicates);

FIG. 2E shows the ratio between the cytosolic and mitochondrial 1C metabolic flux towards purine and pyrimidine biosynthesis inferred based on computational Metabolic Flux Analysis (MFA). Black circle represents the most likely flux ratio and whisker represents the 95% confidence interval of the flux ratio.

FIG. 3A shows fractional labeling of dTTP (the sum of dTTP M+1 and M+2) when feeding cells with [2,3,3-$^2$H]-serine in high and physiological media folate levels (Data are mean±SD, n=3 independent biological replicates);

FIG. 3B shows cell doubling time in high and physiological folate media (Data are mean±SD, n=3 independent biological replicates);

FIG. 7A the Pearson correlation (x-axis) and p-value (y-axis) between the expression of 1C metabolic genes (based on data from the Cell Line Encyclopedia Collection; CCLE) and the cytosolic over mitochondrial 1C flux ratio under physiological folate concentration in the cell lines shown in FIG. 2A, the dashed line representing the significance cut-off based on Bonferroni correction for multiple hypotheses testing;

FIG. 7B shows SLC19A1 expression level by RT-qPCR (x-axis) versus the cytosolic over mitochondrial 1C flux ratio (y-axis) in different cell lines:

FIG. 7C shows RT-qPCR measured expression of SLC19A1 in different cell lines under high and physiological folate condition;

FIG. 7D shows expression of SLC19A1 in A549 control and A549 RFC overexpressing (OE) cells by RT-qPCR (***P<0.001 by two-sample t-test. Data are mean±SD, n=3 independent biological replicates):

FIG. 7E shows cytosolic over mitochondrial 1C flux ratio in A549 control and A549 RFC OE cells under high and physiological folate media (n.s. not significant. ***P<0.001 by two-sample t-test. Data are mean±SD, n=3 independent biological replicates);

FIG. 7F shows the percentage labeling of intracellular proline when feeding A549 control and A549 RFC OE cells with [2,3,3-2H]-serine in physiological folate media (***P<0.001 by two-sample t-test. Data are mean±SD, n=3 independent biological replicates);

FIG. 7G shows relative pool sizes of THF and 10-formyl-THF in A549 control and A549 RFC OE cells under physiological folate media (***P<0.001 by two-sample t-test. Data are mean±SD, n=3 independent biological replicates);

FIG. 7H shows expression of SLC19A1 in HCT16 control and HCT116 RFC KD cells by RT-qPCR (***P<0.001 by two-sample t-test. Data are mean±SD, n=3 independent biological replicates);

FIG. 7I shows cytosolic over mitochondrial 1C flux ratio in HCT116 control and HCT116 RFC KD cells under physiological folate media (n.s. not significant. P<0.01 and *P<0.001 by two-sample t-test. Data are mean±SD, n=3 independent biological replicates):

FIG. 7J shows the percentage labeling of intracellular proline when feeding HCT116 control and HCT116 RFC KD cells with [2,3,3-2H]-serine in physiological folate media (**P<0.01 by two-sample t-test. Data are mean±SD, n=3 independent biological replicates);

FIG. 7K shows relative pool sizes of THF and 10-formyl-THF in HCT116 control and HCT116 RFC KD cells under physiological folate media (***P<0.001 by two-sample t-test. Data are mean±SD, n=3 independent biological replicates);

FIG. 10A shows an in vitro growth assay for WT and SHMT1 KO A549 cells in high and physiological folate media (y-axis showing the relative growth rate in KO versus in WT cells, mean±SD, n=3 independent biological replicates. ***P<0.001 by two-sample t-test);

FIG. 10B shows western blot validation of CRISPR-Cas9 knockout of SHMT1;

FIG. 10C shows in vitro growth assay for control and SHMT1 KO HCT116 cells in high or physiological folate media (y-axis showing the relative growth rate in KO versus in control cells) (n.s. not significant by two-sample t-test. Data are mean±SD, n=3 independent biological replicates);

FIG. 10D shows fraction of control and SHMT1 KO HCT116 cells in S phase when grown in high and physiological folate media (n.s. not significant by two-sample t-test. Data are mean±SD, n=3 independent biological replicates);

FIG. 10E shows ratio between intracellular dUMP and dTTP in control and SHMT1 KO HCT116 cells grown in high and physiological folate media (n.s. not significant. *P<0.05 by two-sample t-test. Data are mean±SD, n=3 independent biological replicates):

DESCRIPTION OF THE INVENTION

Materials and Methods

Figure 4A:
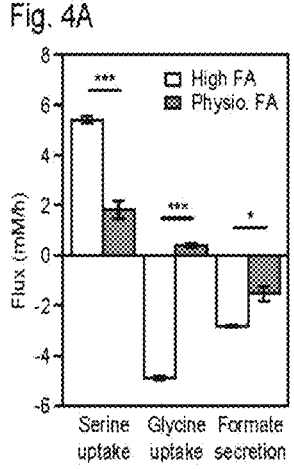
FIG. 4A shows the measured uptake/secretion rate of serine, glycine, and formate in Jurkat in high and physiological media folate levels (*$P<0.05$ and ***$P<0.001$ by two-sample t-test. Data are mean±SD, n=3 independent biological replicates)

Antibodies were as follows: anti-SHMT1 (Cell Signaling Technology, CST-80715S, 1:250), anti-SHMT2 (Sigma, HPA020549, 1:250), anti-MTHFD1 (Santa Cruz Biotechnology, sc-271412, 1:1000), anti-MTHFD1L (Proteintech, 16113-1-AP, 1:1,000), anti-MTHFD2 (GeneTex, GTX104990, 1:1,000, and anti-GAPDH (EMD Millipore, CB10001, 1:10,000). IRDye 680RD goat anti-rabbit (926-68071, 1:15,000) and IRDye 800CW goat anti-mouse (926-32210, 1:15,000) secondary antibodies were from LI-COR. Folic acid (F8758) and sodium formate (71540) were purchased from Sigma. 5-methyltetrahydrofolic acid (16159) and (6S)-tetrahydrofolic acid (18263) were purchased from Cayman Chemical. [1-$^{14}$C]-glycine (MC-1109) was from Moravec and [3-$^{14}$C]-serine (NEC827050UC) was from Perkin-Elmer. [2,3,3-$^{2}$H]-serine (DLM-582), [3-$^{14}$C]-serine (CLM-1572), and [1,2-$^{13}$C$_2$] glycine (CLM-1017) were purchased from Cambridge Isotope Laboratories.

Cell Culture.

All cells were obtained from ATCC while CEM-7A cells (Rothem et al., 2002) were the gift of Prof. Yehuda G. Assaraf (Technion). None of the cell lines used here are listed in the database of commonly misidentified cell lines maintained by ICLAC and NCBI Biosample. All cell lines were confirmed to be *mycoplasma* free by EZ-PCR *Mycoplasma* Test Kit (Biological Industries, 20-700-20). Cell lines were grown in RPMI 1640 (Biological Industries) supplemented with 10% (v/v) heat-inactivated dialyzed fetal bovine serum (Sigma), 2 µM or 200 nM folic acid, 100 U/ml penicillin, and 100 µg/ml streptomycin in a 5% CO$_2$ incubator at 37° C.

Generation of Knockout Cell Lines Using CRISPR-Cas9.

Heterogeneous knockout cell populations were generated using lentiCRISPR v2 (Addgene catalog number 52961). sgRNA against SHMT1 (GAACGGGGCGTATCTCATGG (SEQ ID NO:1)) was designed based on a previous study (Pacold et al., 2016). For sgRNA cloning, lentiCRISPR v2 vector was digested with BsmBI (NEB-R0580S) and ligated with the sgRNA using Quick Ligation™ Kit (NEB-M2200L). From the ligation, 5 µl of the reaction was transformed into 50 µl of Stbl3 bacteria. The bacteria were incubated for 30 min on ice, heat-shocked at 42° C. for 45 seconds, quickly placed on ice for 1-2 min, and then grown at 37° C. for 1 h with 150 µl LB media. After being plated on ampicillin (100 µg/ml) plates for 16 h, bacterial colonies were picked and grown in 2 ml LB media plus ampicillin (100 µg/ml) for 24 h. Plasmid DNA was extracted using the NucleoSpin Plasmid EasyPure kit (MAN-740727.250). The DNA was then sent for sequencing using the U6 primer (sequence: 5' CATATTTGCATATACGATACAAGGCTC 3'(SEQ ID NO:2)) to check the correct insertion of the sgRNA in the lentiCRSPR.v2 vector.

To generate active lentivirus, 3.5×10$^6$ 293T cells were first seeded in 100 mm plates and transfected the following day using a 4:2:1 ratio of lentiCRISPR v2:psPAX2 (Addgene catalog number 12260):pMD2.G (Addgene catalog number 12259) using PEI (DNA:PEI=1:3). Media were changed the next day. 72 h post transfection, media were collected and passed through a 0.45 µm sterile filter.

For cell transduction, 1×10$^6$ Jurkat cells per well were seeded in 96-well U-bottom microtiter plates and immediately pelleted by centrifugation (500 g, 4° C., 3 min). After removing the supernatant, 100 µl of the viral solution was added to each well to transduce the recipient cells in a final polybrene concentration of 10 µg/ml. After 7-9 h, cells were transferred to 6-well plates with 2 ml fresh media per well. For A549 and HCT116 cells, 2.5×10$^5$ cells were seeded in a 6-well plate. After 24 h, 100 µl of the viral solution was added to the cells and polybrene was added to a final concentration of 10 µg/ml. Media were changed after 24 h. Transduced cells were selected using 2 µg/ml puromycin for 72 h and subjected to single-cell cloning by limiting dilution in 96 well plates.

Generation of A549 Cells with RFC Overexpression.

A549 cells overexpressing RFC were generated using FUGW vector (Addgene #14883). SLC19A1 cDNA (NM_194255.4) was cloned inside FUGW vector upon addition of AgeI and BamHI restriction sites via PCR using Phusion High-Fidelity DNA polymerase (NEB-M0530S). FUGW vector and cDNA were subsequently digested with AgeI and BamHI and ligated with Quick Ligation™ Kit (NEB-M2200L). Bacteria transformation, lentiviral production, and viral transduction of A549 were carried out as described above. A549 cells infected with FUGW or FUGW-RFC were sorted using FACS Aria Illu (Becton Dickinson) as follows: 2×106 cells were resuspended in PBS/2% PSA and EGFP positive cells were collected in 15 ml tubes containing 3 ml of FBS/2% PSA. Sorted cells were then spun down and resuspended in appropriate amount of media.

Generation of HCT116 Cells with RFC Knockdown.

Lentivirus production and viral transduction of HCT116 cells were performed as described above. shRNAs targeting SLC19A1 (RFC1) had sequences of CCGGCGACGGTGTTCAGAATGTGAACTCGAGTT-CACATTCTGAACACCGT CGTTTTTG (SEQ ID NO:3) (TRCN0000043129) or CCGGCCGCAAGCAGTTCCAGT-TATACTCGAGTATAACTGGAACTGCTTGC GGTTTTTG (SEQ ID NO:4) (TRCN0000043131). For control, pLKO.1 scrambled Mission control vector (Sigma) was used.

Quantitative PCR.

Total RNA was extracted from different cell lines using TRIzol (Thermo, 15596026) according to the manufacturer's instructions. The RNA was then treated with RQI Rnase-free Dnase (Promega, M6101) to remove DNA contamination. Reverse transcription was carried out with qPCRBIO cDNA Synthesis Kit (PCR Biosystems, PB30.11-10), using 0.4 μg of total RNA. The reactions were incubated for 30 min at 42° C. followed by 10 min inactivation incubation at 85° C. Quantitative PCR reactions were run on a 96-well CFX96 Touch™ Real-Time PCR Detection System (Biorad), using 10 μl of 2× qPCRBIO SyGreen Blue Mix (PCR Biosystems, PB20.15) and 2 μM forward and reverse primers in a final volume of 20 μl. All reactions were performed in triplicates in the following conditions: pre-heating at 95° C. for 10 min, followed by 40 cycles of 10 sec at 95° C., 10 sec at 60° C., and 10 sec at 72° C. The rps11 and tpt1 were used as reference genes. Primer sequences are:

```
SLC19A1
Forward:
                                      (SEQ ID NO: 5)
CCTCGTGTGCTACCTTTGCTT Reverse:
                                      (SEQ ID NO: 6)
TGATCTCGTTCGTGACCTGCT RPS11
Forward:
                                      (SEQ ID NO: 7)
CCGAGACTATCTGCACTACATCC Reverse:
                                      (SEQ ID NO: 8)
GTGCCGGCAGCCTTG TPT1
Forward:
                                      (SEQ ID NO: 9)
CACCTGCAGGAAACAAGTTTC Reverse:
                                      (SEQ ID NO: 10)
GTCACACCATCCTCACGGTAG
```

Immunoblotting.

For protein extracts, cells were lysed in ice-cold Triton lysis buffer (40 mM HEPES, pH 7.4, 120 mM NaCl, 1 mM EDTA, 1% TritonX-100, 10 mM sodium pyrophosphate, 10 mM glycerol 2-phosphate, 50 mM NaF, 0.5 mM sodium orthovanadate, 1 μM Microcystin-LR, 0.2 mM PMSF and protease inhibitor cocktail) for 30 min, followed by an overnight Benzonase treatment (Merck, E1014) at 4° C. Protein concentrations were determined with Pierce™ BCA Protein Assay Kit (Thermo, 23225). Protein lysates were normalized for each experiment and equal amounts of protein were loaded into each lane of 10% SDS polyacryl-amide gels. Proteins were separated by SDS-PAGE, transferred to nitrocellulose membranes and incubated overnight at 4° C. with indicated primary antibodies. Infrared western blot assay was performed using Odyssey Fc Imaging System or Odyssey CLx Imaging System (LI-COR Biosciences).

Proliferation Assay.

$2 \times 10^4$ cells per well were seeded in 24-well plates. For the 1-week growth assay, half of the media was replaced on day 3. Cell number was measured via a Multisizer Coulter Counter (Beckman Coulter).

Flow cytometry.

$1 \times 10^6$ cells were washed twice and resuspended in 300 μl PBS. To the cell suspension, 700 μl of pre-chilled (−20° C.) 70% EtOH was added dropwise while vortexing. The samples were incubated on ice for 30 min, washed twice, resuspended in 300 μl PBS, and propidium iodide (PI) was added at a final concentration of 20 μg/ml. Cells were analyzed with the BD LSR-II Analyzer (BD) using a 488 nm blue laser and 575/26 filter. An unstained fixed sample was used to set the proper parameters. Cell cycle analysis was performed using the ModFit LT 5.0 software (Verity Software House).

RNA-seq Profiling.

Tumor cells were analyzed after being acclimated to high or physiological folate medium for at least two weeks. RNA was isolated using Trizol and mRNA libraries were prepared using the TruSeq RNA Library Preparation kit v2 (Illumina). cDNA libraries were sequenced on an Illumina HiSeq2500 to obtain >50-bp single-end sequence reads. Reads were aligned to the GRCh37 human reference genome using TopHat (2.1.0) (Trapnell et al., 2009). Up to 3 mismatches were allowed per read, with up to 2 mismatches per segment. Gene counts were obtained using HTSeq-count (0.6.1) (Anders et al., 2015). The counts normalization and the differential expression analysis were done using the DESeq2 package version 1.18.1 (Love et al., 2014). Library preparation and sequencing procedures were performed at the Technion Genome Center (Haifa, Israel). The RNA-seq data have been deposited in NCBI's Gene Expression Omnibus and are accessible through GEO Series accession number GSE153023 (https://www.ncbi.nlm.nih.gov/geo/query/acc.cgi?acc=GSE153023).

Isotope tracing.

Isotope tracing was performed by feeding exponentially growing cells with [2,3,33-$^2$H]-serine. Cells were fed with labeled substrates for 24 h and metabolism was quenched immediately by adding −80° C. 50:30:20 (v/v/v) methanol: acetonitrile:water. Metabolite samples were stored at −80° C. until analysis. LC-MS was used to measure the mass-isotopomer distribution of metabolites. Measured mass-isotopomer distributions were corrected for natural abundance (Millard et al., 2012).

LC-MS Analysis.

Chromatographic separation was achieved on a SeQuant ZIC-pHILIC column (2.1×150 mm, 5 μm, EMD Millipore). Flow rate was set to 0.2 ml/min, column compartment was set to 30° C., and autosampler tray maintained 4° C. Mobile phase A consisted of 20 mM ammonium carbonate and 0.01% (v/v) ammonium hydroxide. Mobile Phase B was 100% acetonitrile. The mobile phase linear gradient (% B) was as follows: 0 min 80%, 15 min 20%, 15.1 min 80%, 23 min 80%. A mobile phase was introduced to Thermo Q Exactive mass spectrometer with an electrospray ionization source working in polarity switching mode. Ionization source parameters were following: sheath gas 25, auxiliary gas 3, spray voltage 3.3 and 3.8 kV in negative and positive ionization mode respectively, capillary temperature 325° C., S-lens RF level 65, auxiliary gas temperature 200° C. Metabolites were analyzed in the range 72-1080 m/z. Positions of metabolites in the chromatogram were identified by corresponding pure chemical standards. Data were analyzed with MAVEN (Melamud et al., 2010). Absolute metabolite pool sizes were quantified using isotope-ratio with chemical standards (Bennett et al., 2008). Intracellular folate and THF levels were measured as described previously (Chen et al., 2017).

NMR Detection of Formate.

Suspension cells (packed cell volume=10 μl) under exponential growth were collected and resuspended in T-75 flasks with 15 ml of fresh medium. After 24 h, 12 ml of spent medium was carefully collected post centrifugation (800 g, 5 min), and immediately mixed with 38 ml of −80° C. 50:30 (v/v) methanol:acetonitrile. After a brief vortex, samples were centrifuged (15,000 g, 30 min, 4° C.) and 50 ml of supernatant was dried by lyophilization. Dried samples were resuspended in 600 µl D2O. Proton spectra were acquired on a Bruker Avance II 400 MHz NMR Spectrometer with 30-degree excitation pulses (zg30 program), 128 scans per sample. Data were analyzed using TopSpin 4.0.7 software. Formate proton showed a singlet peak with a chemical shift of 8.53 ppm. Absolute quantification of formate was achieved using the standard curve method (fresh media with formate standard additions were processed as above to generate the standard curve). All reactions were performed in biological triplicates. Formate excretion rate was calculated as previously described (Jain et al., 2012).

In Vivo Xenograft Experiment.

All animal experiments were approved by the Animal Care Committee of the Technion (Haifa, Israel). For tumor growth studies, WT or SHMT1 knockout cells ($1 \times 10^6$ cells in 200 µl 50% Matrigel) were injected in the rear flank of NOD/SCID mice and tumor growth was inspected over time using two caliper measurements (volume=½ [L×W2]). For tumor metabolomic studies, NOD/SCID mice were bilaterally injected on the rear flank with WT (right) and SHMT1 mutant cells (left) ($3 \times 10^6$ cells in 100 µl PBS). Mice were sacrificed when control tumors had achieved an average size of ~100 mg (~5 mm) to avoid the development of tumor necrosis. Tumors were removed and immediately frozen in liquid nitrogen for LC-MS analysis. Isolated tumors were weighed, then 40 mg tissue was disrupted and lysed using TissueLyser II (Qiagen) and −80° C. 50:30:20 (v/v/v) methanol:acetonitrile:water. Metabolite samples were stored at −80° C. until analysis.

$CO_2$ Release Measurement.

Radioactive carbon dioxide release was measured via feeding cells with [3-$^{14}$C]-serine and [1-$^{14}$C]-glycine. Cells were grown in 12.5 cm flasks in 2 ml of medium. Flasks were sealed with gas-tight rubber stoppers. Each flask was equipped with a central well containing 4×4 mm filter paper soaked in 20 µl of concentrated KOH solution at ~60° C. Media for tracing experiments were prepared by mixing a complete RPMI medium with 0.750 µCi [1-$^{14}$C]-glycine or 0.375 µCi [3-$^{14}$C]-serine. The exact amount of radioactive tracers was verified in each experiment by measuring scintillation in unused media. After 12 h, metabolism was terminated by adding sulfuric acid to the final concentration 1 N via injecting the stock solution with a needle through a rubber stopper. After 1 h, the content of central wells was transferred to scintillation vials with 10 ml of Perkin-Elmer Ultima Gold® liquid scintillation cocktail, and scintillation was recorded on Perkin-Elmer Tri-Carb 2810 TR scintillation analyzer. Cell volume measurements and stable isotope tracing with [3-$^{13}$C]-serine and [1,2-$^{13}$C$_2$] glycine were performed for non-radioactive cells growing in parallel in conditions as described above. Cell volume was measured with Beckman-Coulter Z2 Particle Counter at the beginning and the end of the experiment and the average PCV was calculated via approximation of the exponential growth. For stable isotope labeling analysis, cells were washed with PBS once, and metabolites were extracted with 50:30:20 (v/v/v) methanol:acetonitrile:water. Metabolite extracts were analyzed with LC-MS. Carbon dioxide release flux was quantified as previously described (Fan et al., 2014).

Metabolic Flux Analysis (MFA).

We employ stationary-MFA for estimating cytosolic and mitochondrial 1C fluxes based on [2,3,3-$^2$H]-serine tracing experiments. The method received as input the isotopic labeling of intracellular serine, glycine, and dTTP, under isotopic steady state, the net uptake and secretion rates of glycine, serine, and formate, and cellular demand of 1C units for purine and pyrimidine biosynthesis (Tables 1-4). To achieve isotopic steady state, $1 \times 10^6$ cells under exponential growth were collected and resuspended in T-75 flasks with 40 ml of fresh RPMI 1640 (Biological Industries) supplemented with 10% (v/v) heat-inactivated dialyzed fetal bovine serum (Sigma), 2 µM or 200 nM folic acid, 30 mg/L [2,3,3-$^2$H]-serine, 100 U/ml penicillin, and 100 µg/ml streptomycin in a 5% CO2 incubator at 37° C. for 24 h (media serine and glycine labeling did not change 24 h post cell seeding as shown in Table 3). We formulate a non-convex optimization, searching for the most likely cytosolic and mitochondrial 1C fluxes under isotopic steady state (denoted v, see network model in FIG. 1), such that simulated labeling of metabolite m (serine, glycine, or dTTP) in mitochondria YMIT,m and cytosol (YCYT,m) match metabolite isotopic labeling measurements performed on a whole-cell level (Xim); computing the expected whole-cell labeling by convolution of the simulated mitochondrial and cytosolic labeling patterns:

$$\sum_{m \in \{ser,gly,dTTP\}} \sum_{i=0}^{N_m} \left( \frac{X_i^m - \begin{pmatrix} \alpha_m * Y_i^{MIT,m}(v) + \\ (1-\alpha_m) * \\ Y_i^{CYT,m}(v) \end{pmatrix}}{\sigma_i^m} \right)^2 + \sum_{j=1}^{N} \left( \frac{v_j -}{\sigma_j} u_j \right)^2$$

s.t.

$Sv = 0$ Stoichiometric mass balance $v_{lb} \leq v \leq v_{ub}$ Lower and upper bound on 1C demand fluxes $0 \leq \alpha_{ser} \leq 1$ Cytosolic to mitochondrial metabolite pool size ratios $0 \leq \alpha_{gyl} \leq 1$ $\alpha_{dTP} = 1$ where S denotes a stoichiometric matrix ($S_{i,j}$ representing the stoichiometric coefficient of metabolite i in reaction j), and vlb and vub denote lower and upper bounds on fluxes based on uptake and secretion rates and estimated cellular demand for cell proliferation. Cellular demand for 1C units was estimated based on growth rate and biomass composition. Specifically, demand of methylene-THF (0.76 mM/h) was estimated based on DNA content of 0.025 ng/cell (Fan et al., 2014), measurement of cell volume ($1.2 \times 10^6$ CCRF-CEM cells/µl), and doubling time of 20 h: and a demand for 10-formyl-THF (6.9 mM/h) assuming cellular RNA/DNA mass ratio of 1.3 (Ducker et al., 2016; Fan et al., 2014) (setting the lower and upper bounds on the corresponding reactions to within 10% of the estimated demand fluxes). The $i^{th}$ mass-isotopomer of metabolite m mitochondria and in cytosol, denoted YiMIT,m and YiCYT,m, respectively, were uniquely determined via the Elementary Metabolite Unit (EMU) approach (Antoniewicz et al., 2007). The whole-cell level mass-isotopomer distribution of metabolite m was simulated via convolution of the corresponding mitochondrial and cytosolic distributions, considering a ratio between the metabolite pool size in cytosol and mitochondria (denoted by $\alpha_m$), determined by the optimization (considering a potential difference in the labeling of serine and glycine in mitochondria and cytosol; and dTTP existing only in the cytosol; dTTP=1). The objective function searches for a maximum log-likelihood estimation of fluxes; minimizing the variance-weighted sum of squared residual of the differences between: (i) the mass-isotopomer distribution of metabolites measured on a whole-cell level and a convolution of the simulated mitochondrial and cytosolic mass-isotopomer distributions (im denotes the standard deviation in the $i^{th}$ measured mass-isotopomer of metabolite m; Nm denotes the number of carbons in metabolite m); as well as, (ii) measured and simulated metabolite uptake and secretion rates (j denotes the standard deviation in the measurement of metabolite uptake or secretion rate through reaction j). The non-convex optimization problem was solved using MATLAB's Sequential Quadratic Optimization (SQP), starting from 100 sets of random fluxes to overcome potential local minima. To compute confidence intervals for the ratio of SHMT1 and SHMT2 flux, SQP was iteratively run to compute the maximum log-likelihood estimation while constraining the flux ratio to increasing (and then decreasing) values (with a step size equal to 5% of the fluxes ratio predicted in the initial maximum log-likelihood estimation)(Antoniewicz et al., 2006; Fan et al., 2013b). Confidence interval bounds were determined based on the 95% quantile of $\chi2$-distribution with one degree of freedom. MFA code is available via GitHub at https://github.com/stemal75/compartmentalized_mfa.git.

Results

A Variety of Cancer Cells Switch to Relying Mostly on Cytosolic 1C Flux Under Physiological Folate Levels To examine the relative contribution of the cytosolic versus mitochondrial folate cycle to pyrimidine biosynthesis under physiological folate levels, which is in the range of 150-450 nM in human serum (Fazili et al., 2008; Wishart et al., 2018), stable isotope tracing was performed across a panel of human cancer cell lines. Cells were fed [2,3,3-$^2$H]-serine and the incorporation of deuterium labeling in synthesized thymidine triphosphate (dTTP) was monitored. As shown in FIG. 2A, lowering the total folate concentration in culture media to a physiological level (from 2.2 μM as in RPMI to 200 nM) led to about a 10-fold increase, on average, in the relative contribution of the cytosolic folate cycle for pyrimidine biosynthesis across different cell lines (dTTP M+2/M+1). Under physiological folate, the cytosolic pathway became the predominant contributor for 1C units in tumors of various origins (dTTP M+2/M+1>1; FIG. 3A), including T-cell acute lymphoblastic leukemia, glioblastoma, and non-small-cell lung carcinoma. Notably, media folate levels had no effect on the cell growth rate, suggesting cytosolic 1C flux is sufficient to meet anabolic demands under physiological folate conditions (FIG. 3B).

Figure 4B:
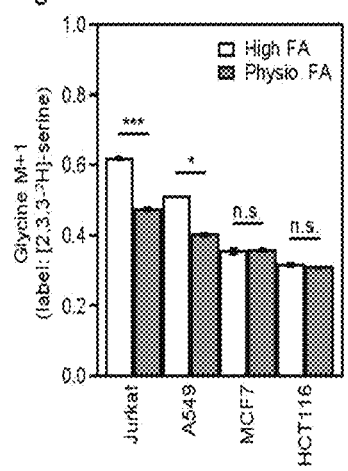
FIG. 4B shows the fractional labeling of intracellular glycine when feeding cells with [2,3,3-$^2$H]-serine in high and physiological media folate levels (n.s. not significant. *$P<0.05$ and ***$P<0.001$ by two-sample t-test. Data are mean±SD, n=3 independent biological replicates)
Figure 4C:
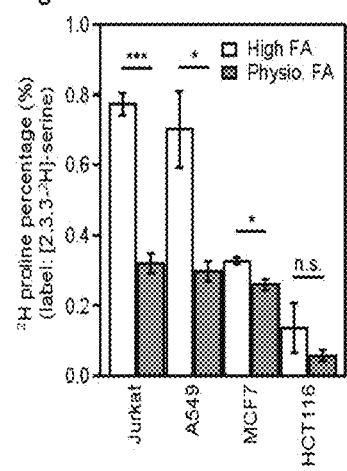
FIG. 4C shows the percentage labeling of intracellular proline when feeding cells with [2,3,3-$^2$H]-serine in high and physiological media folate levels (n.s. not significant. *$P<0.05$ and ***$P<0.001$ by two-sample t-test. Data are mean±SD, n=3 independent biological replicates)

The increased reliance on SHMT1 for producing 1C units under physiological folate conditions was associated with a drop in whole-cell SHMT flux, suggesting a marked decrease specifically in SHMT2 flux. Reduced whole-cell SHMT flux was evident by about a 5-fold decrease in serine consumption from culture media in CCRF-CEM cells grown in physiological versus high folate conditions (p-value<0.001; FIG. 2B); and a consistent drop in the secretion of the two products, glycine and formate. While glycine was excreted under high folate media, substantial glycine uptake flux was observed under physiological folates (~0.8 mM/h; ~50% of serine uptake). Increased cellular reliance on extracellular glycine versus de novo production from serine was further evident by a significant decrease in glycine M+1 when feeding [2,3,3-$^2$H]-serine under high versus physiological folate media (p-value<0.001; FIG. 2C). Formate secretion rate showed a significant ~7-fold reduction under physiological folate (p-value<0.001; FIG. 2B). A decrease in mitochondrial 1C flux under physiological folate condition was further evident by a drop in the contribution of serine catabolism to the reduction of mitochondrial NADP+ via methylenetetrahydrofolate dehydrogenase 2 (MTHFD2). Proline biosynthesis involves oxidation of mitochondrial NADPH, hence its labeling represents the contribution of serine catabolism to NADPH production. Feeding [2,3,3-$^2$H]-serine under physiological folate significantly lowered the fractional deuterium labeling of proline (p-value<0.001; FIG. 2D) synthesized in mitochondria by δ-1-pyrroline-5-carboxylate synthase (ALDH18A1), oxidizing NADPH and transferring hydrogen to the proline precursor L-glutamate-5-semialdehyde (Ducker et al., 2016). [This last sentence needs to be ironed out a bit] A similar significant decrease in mitochondria-derived 1C flux was found in Jurkat and A549 when switched to physiological folate conditions, primarily relying on cytosolic 1C flux (FIG. 4). These results suggest that while 'overflow metabolism' in mitochondrial serine catabolism appears in some cancer cells under physiological folate and in vivo (Meiser et al., 2016, 2018), it is not a ubiquitous hallmark of all tumors.

Figure 5:
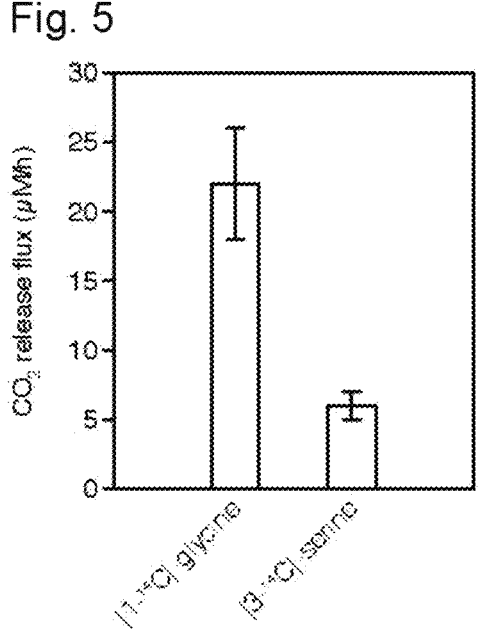
FIG. 5 shows $CO_2$ release fluxes (μM/h) in CCRF-CEM.

A potential bias in the interpretation of the cytosolic versus mitochondrial 1C flux based on [2,3,3-$^2$H]-serine tracing is due to isotope exchange effects, where enzymes near chemical equilibrium simultaneously catalyze flux in the forward and backward directions (Fan et al., 2013a). To overcome this and quantitatively infer cytosolic and mitochondrial net fluxes, a variant of metabolic flux analysis (MFA) was employed, modeling compartmentalized fluxes based on [2,3,3-$^2$H]-serine tracing experiments. This analysis searches for the most likely cytosolic and mitochondrial fluxes such that whole-cell level measured isotopic labeling of serine and glycine match a convolution of the simulated labeling of these metabolites in the two compartments (Tables 1-4). Measured $CO_2$ release fluxes (μM/h) in CCRF-CEM are orders of magnitude lower than serine and glycine exchange and were hence omitted from the MFA analysis (FIG. 5). This analysis further supports the cytosolic folate pathway in CCRF-CEM being the major net contributor of 1C units for pyrimidine biosynthesis under physiological folates (FIG. 2E).

Figure 6A:
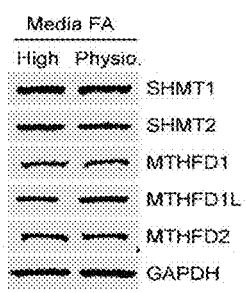
FIG. 6A shows a western blot of 1C enzymes in Jurkat cells under high and physiological media folate.
Figure 6B:
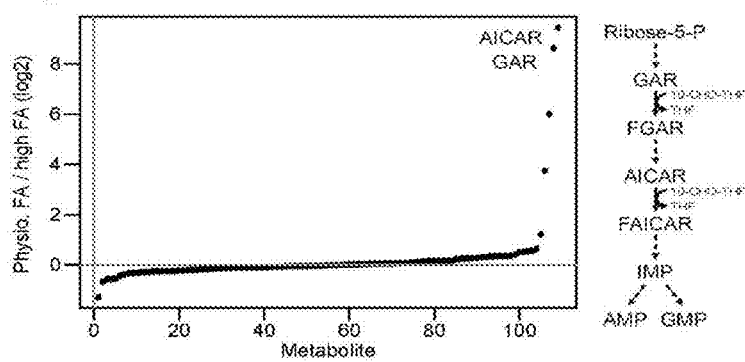
FIG. 6B shows the ratio between intracellular metabolite concentrations in Jurkat cells grown in physiological and high folate media.
Figure 6C:
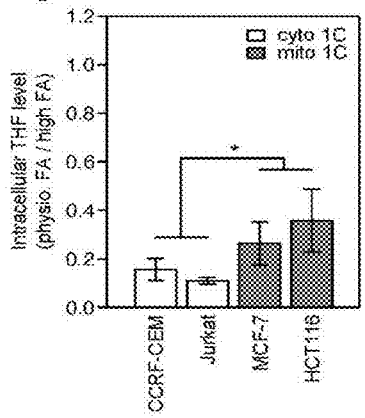
FIG. 6C shows intracellular THF levels in high and physiological media folate (*$P<0.05$ by two-sample t-test. Data are mean±SD, n=3 independent biological replicates)
Figure 6D:
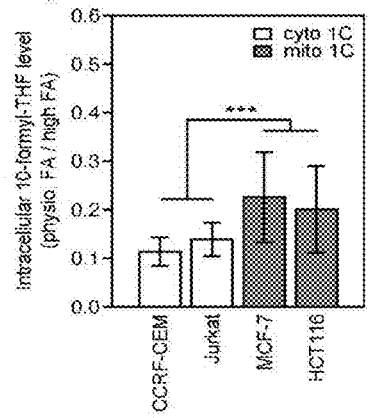
FIG. 6D shows intracellular 10-formyl-THF levels in high and physiological media folate (***$P<0.001$ by two-sample t-test. Data are mean±SD, n=3 independent biological replicates)
Figure 6E:
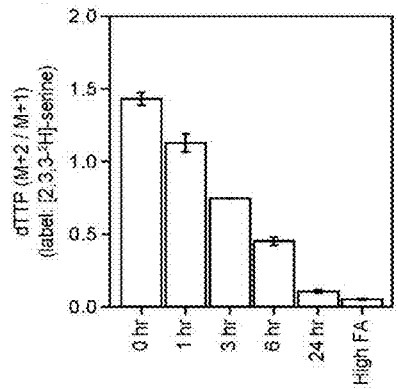
FIG. 6E shows measured dTTP M+2/M+1 in Jurkat cells fed with [2,3,3-$^2$H]-serine, when switched from physiological to high folate media.
Figure 12A:
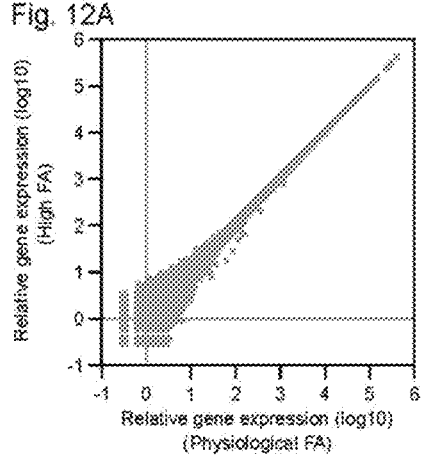
FIG. 12A shows global gene expression in CCRF-CEM cells under high and physiological folate measured via RNAseq.
Figure 12B:
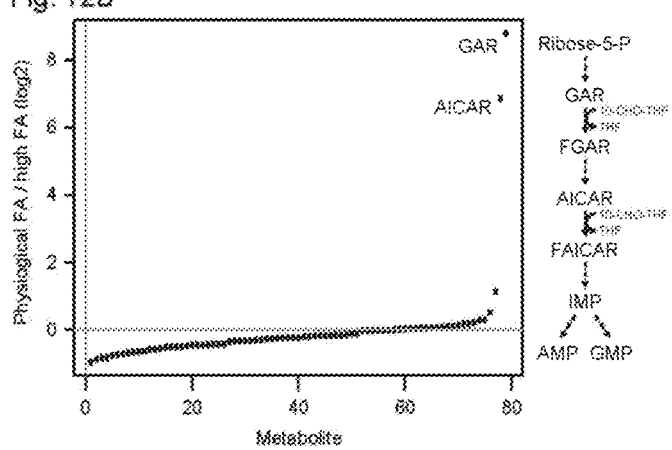
FIG. 12B shows the ratio between intracellular metabolite concentrations in CCRF-CEM cells grown in physiological and in high folate media.

Cytosolic Versus Mitochondrial 1C Flux is Regulated by SLC19A1, Modulating Intracellular Folate Levels Exploring how cells regulate cytosolic versus mitochondrial 1C flux in response to folate availability, it was found that media folate level had no effect on the concentration of key 1C metabolic enzymes in Jurkat cells (FIG. 6A); or an effect on the global mRNA expression pattern (FIG. 12A). Metabolomics analysis using liquid chromatography-mass spectrometry (LC-MS), revealed a significant (>50-fold) increase in the intracellular concentrations of the purine biosynthesis intermediates 5'-phosphoribosyl-5-aminoimidazole-4-carboxamide (AICAR) and 5'-phosphoribosyl-glycinamide (GAR) in cells under physiological folate (FIGS. 6B and 12B), indicating a potential drop in intracellular folate pools (Ducker et al., 2016). Indeed, the intracellular concentrations of THF and 10-formyl-THF in Jurkat and CCRF-CEM showed a significant 80-90% decrease while switching primarily to the cytosolic 1C flux under physiological folate conditions (FIGS. 6C and 6D). In comparison, MCF-7 and HCT116 that primarily rely on mitochondrial 1C flux under physiological folate conditions showed a higher capacity to retain intracellular folates, showing a significantly smaller drop in the concentration of THF and 10-formyl-THF (p-value<0.01; FIGS. 6C and 6D). These results suggest substrate-level down regulation of mitochondrial 1C flux in Jurkat and CCRF-CEM under physiological folate due to the depletion of intracellular reduced folates. Accordingly, it was found that switching cells back from physiological to high folate media resulted in rapid induction of mitochondrial 1C flux in Jurkat cells (dTTP M+2/M+1 decreased ~16% in 1 h after switching from physiological to high folate media; p-value<0.05; FIG. 6E).

To explore the mechanism underlying cell line-specific reliance on the cytosolic versus mitochondrial 1C flux, the expression levels of 1C genes across the studied cell lines was analyzed utilizing transcriptomic data from the Cell Line Encyclopedia Collection (CCLE) (Klijn et al., 2015). It was found that the expression level of SLC19A1, which encodes the reduced folate carrier (RFC), is significantly lower in cell lines that rely on the cytosolic 1C pathway (FIG. 7A). It was further validated with RT-qPCR that cell lines relying on cytosolic 1C flux have lower expression of SLC19A1 (FIG. 7B); where the expression of SLC19A1 is not affected by the media folate concentration (FIG. 7C). RFC is an anion antiporter that utilizes the phosphate gradient to achieve uphill folate transport into cells and is ubiquitously expressed across tissues (Hou and Matherly, 2014). Note that the expression levels of other folate transporters such SLC46A1 coding for the proton-coupled folate transporter (PCFT) and folate receptors (Frα-FOLR1, Frβ-FOLR2, and Frγ-FOLR3) were not significantly correlated with the cytosolic 1C flux (FIG. 7A). Similarly to SLC19A1, it was found that the expression level of FPGS (folylpolyglutamate synthetase) is significantly lower in cell lines that rely on the cytosolic 1C pathway (FIG. 7A). Low expression of FPGS results in reduced capacity to retain intracellular folates, similarly to low expression of RFC.

Figure 8A:
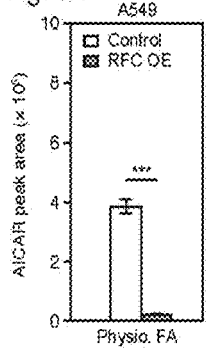
FIG. 8A shows AICAR peak areas in A549 control and A549 RFC OE cells under physiological folate media (***P<0.001 by two-sample t-test. Data are mean±SD, n=3 independent biological replicates)
Figure 8B:
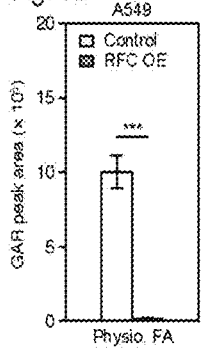
FIG. 8B shows GAR peak areas in A549 control and A549 RFC OE cells under physiological folate media (***P<0.001 by two-sample t-test. Data are mean±SD, n=3 independent biological replicates)
Figure 8C:
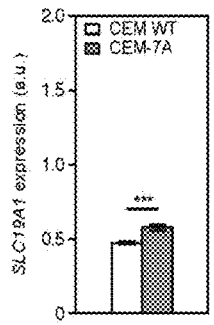
FIG. 8C shows SLC19A1 expression in CCRF-CEM (CEM-WT) and a subline over-expressing RFC (CEM-7A) by RT-qPCR (***P<0.001 by two-sample t-test. Data are mean±SD, n=3 independent biological replicates)
Figure 8D:
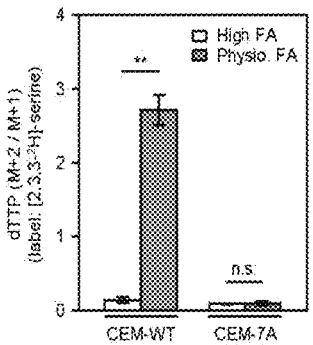
FIG. 8D shows cytosolic over mitochondrial 1C flux ratio in CEM-WT and CEM-7A under high and physiological folate media (n.s. not significant. **P<0.01 by two-sample t-test. Data are mean±SD. n=3 independent biological replicates)
Figure 8E:
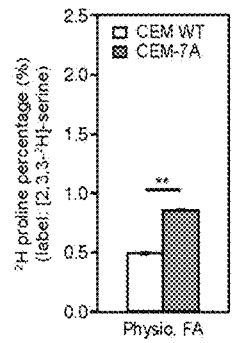
FIG. 8E shows the percentage labeling of intracellular proline when feeding CEM-WT and CEM-7A cells with [2,3,3-$^2$H]-serine in physiological folate media (**P<0.01 by two-sample t-test. Data are mean±SD, n=3 independent biological replicates)
Figure 8F:
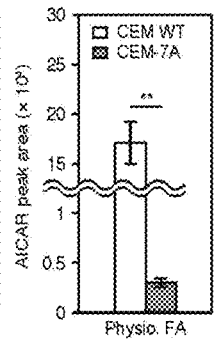
FIG. 8F shows AICAR peak areas in CEM-WT and CEM-7A under physiological folate media (**P<0.01 by two-sample t-test. Data are mean±SD, n=3 independent biological replicates)
Figure 8G:
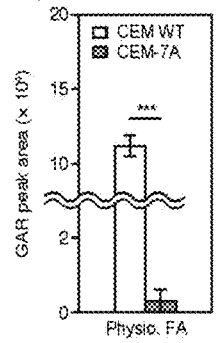
FIG. 8G shows GAR peak areas in CEM-WT and CEM-7A under physiological folate media (***P<0.001 by two-sample t-test. Data are mean±SD, n=3 independent biological replicates)
Figure 8H:
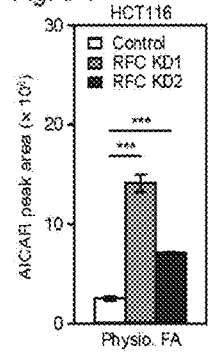
FIG. 8H shows AICAR peak areas in HCT116 control and HCT116 RFC KD cells under physiological folate media (***P<0.001 by two-sample t-test. Data are mean±SD, n=3 independent biological replicates)
Figure 8I:
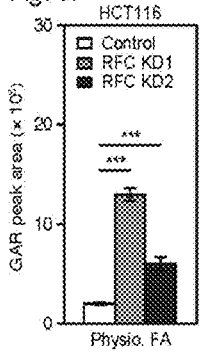
FIG. 8I shows GAR peak areas in HCT116 control and HCT116 RFC KD cells under physiological folate media (***P<0.001 by two-sample t-test. Data are mean±SD, n=3 independent biological replicates)

To test whether the RFC level regulates cytosolic versus mitochondrial 1C flux by modulating intracellular folate levels, SLC19A1 was overexpressed in A549 cells, which rely mostly on cytosolic SHMT1 flux under physiological folate condition (FIG. 7D). Feeding [2,3,3-2H]-serine revealed that SLC19A1 overexpression induced mitochondrial 1C flux, preventing a shift towards cytosolic folate cycle when switching cells from high to physiological folate conditions (dTTP M+2/M+1 is unaffected by media folate levels in cells that overexpress SLC9A1; FIG. 7E). Induced mitochondrial 1C flux upon SLC19A1 overexpression was further evident by a significant increase in the contribution of serine catabolism to the reduction of mitochondrial NADP+ based on proline labeling (p-value<0.001; FIG. 7F). SLC19A1 overexpression increased intracellular folate availability (FIG. 3G), which is also evidenced by a significant drop in AICAR and GAR levels in SLC19A1 overexpressing cells versus control (p-value<0.001; FIGS. 8A and 8B). Similarly, RFC overexpressing CEM-7A cells (Rothem et al., 2002) showed a major shift towards mitochondrial SHMT2 flux and a significant increase in intracellular folate levels compared to their parental CCRF-CEM cells (p-value<0.001; FIGS. 8C, 8D, 8E, 8F and 8G). Analogously, depleting RFC in HCT116 cells that primarily utilize the mitochondrial 1C cycle under physiological folate conditions (FIG. 7H), resulted in the repression of mitochondrial 1C flux and a shift towards cytosolic 1C flux under physiological folate media (p-value<0.01; FIG. 7I). SLC19A1 knockdown in HCT116 resulted in a significant drop in the contribution of serine catabolism to the production of mitochondrial NADPH (p-value<0.001; FIG. 7J). Finally, SLC19A1 depletion lowered intracellular folate availability (FIG. 7K), while increasing the intracellular AICAR and GAR levels (FIGS. 8H-I). Taken together, the results show that RFC modulates the cytosolic versus mitochondrial 1C metabolism by controlling intracellular folate availability.

Cytosolic SHMT1 is Essential for Growth of Low RFC Expressing Jurkat Tumors

Figure 9A:
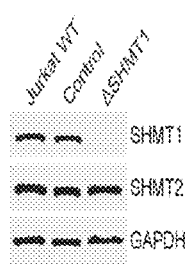
FIG. 9A shows western blot validation of CRISPR-Cas9 knockout of SHMT1.
Figure 9B:
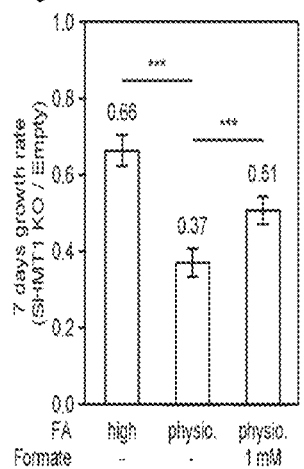
FIG. 9B shows an in vitro growth assay for control and SHMT1 KO Jurkat cells in high folate media, physiological folate media, and physiological folate with formate media (y-axis showing the relative growth rate in KO versus in control cells (***P<0.001 by two-sample t-test. Data are mean±SD, n=3 independent biological replicates)
Figure 9C:
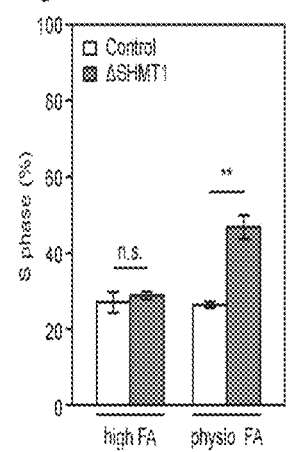
FIG. 9C shows the fraction of control and SHMT1 KO cells in S phase when grown in high and physiological folate media (n.s. not significant. **P<0.01 by two-sample t-test. Data are mean±SD, n=3 independent biological replicates)
Figure 9D:
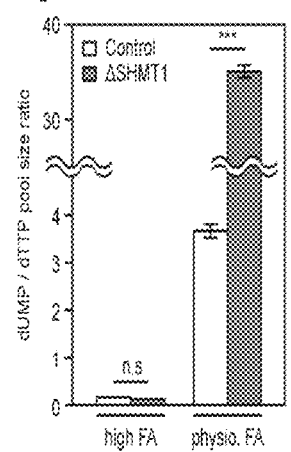
FIG. 9D shows the ratio between intracellular dUMP and dTTP in control and SHMT1 KO cells grown in high and physiological folate media (n.s. not significant. ***P<0.001 by two-sample t-test. Data are mean±SD, n=3 independent biological replicates)
Figure 9E:
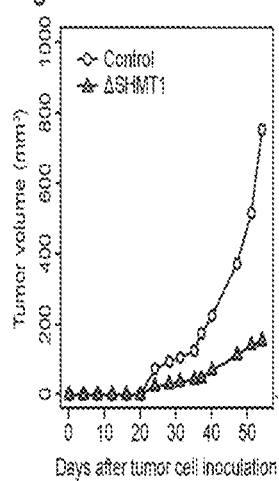
FIG. 9E shows the growth of control and SHMT1 KO Jurkat xenograft (n=8, the bold line representing the average size)
Figure 9F:
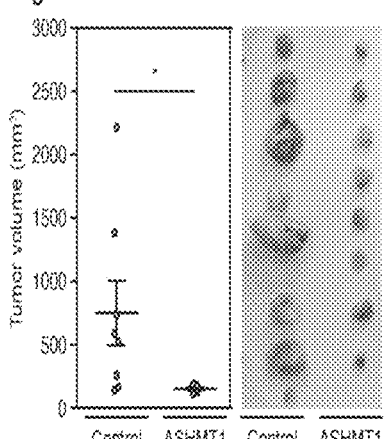
FIG. 9F shows tumors 8 weeks post injection of control (left) and SHMT1 KO (right) Jurkat cells (n=8, *P<0.05; Mann-Whitney U test)

Considering the induced contribution of cytosolic 1C flux to biosynthesis in cancer cells with low RFC expression, whether SHMT1 knockout in these cells hinders tumor growth was tested. It was found that SHMT1-deficient Jurkat cells (FIG. 9A) showed a significant ~65% decrease in growth rate under physiological folate levels (p-value<0.001); a significantly larger decrease in growth rate than that observed in high folate conditions (p-value<0.001; FIG. 9B). A similar drop in growth due to SHMT1 KO was observed in A549 under physiological folate conditions (FIG. 10A). Feeding SHMT1 KO cells with formate partially rescued the impaired growth, suggesting that the mitochondrial folate cycle cannot meet cellular growth demand for 1C units under physiological folate condition (FIG. 9B). The drop in cell proliferation in the SHMT1 KO cells was associated with a significant ~27% increase in the fraction of cells in S phase (p-value<0.01; FIG. 9C) and a significant increase in the dUMP to dTTP ratio (p-value<0.001; FIG. 9D), suggesting insufficient thymidylate synthase (TS) flux to support dTTP production for DNA replication. In contrast to the effect of SHMT1 knockout in low RFC expressing Jurkat cells, SHMT1 knockout in high RFC expressing HCT116 cells had no effect on cell growth rate (FIGS. 10B and 10C) nor on cell cycle (FIG. 10D), and did not lead to an increase in dUMP/dTTP pool size ratio (FIG. 10E).

Figure 9G:
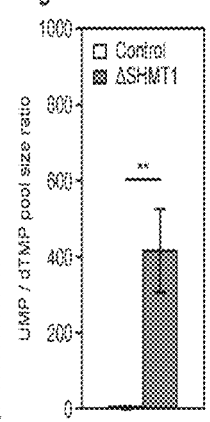
FIG. 9G shows the ratio between intra-tumor UMP and dTMP in control and SHMT1 KO Jurkat xenografts (n=5, **P<0.01 by two-sample t-test. Data are mean±SD)
Figure 9H:
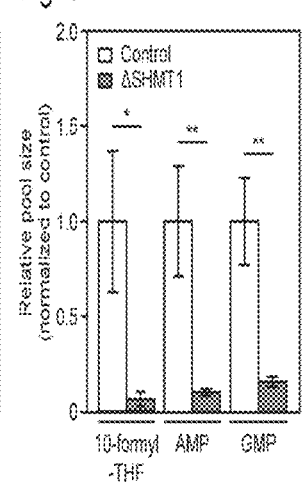
FIG. 9H shows relative pool sizes of 10-formyl-THF, AMP, and GMP in control and SHMT1 KO Jurkat xenografts (n=5, *P<0.05 and **P<0.01 by two-sample t-test. Data are mean±SD)
Figure 11A:
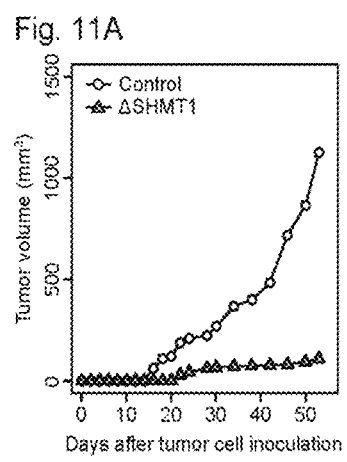
FIG. 11A shows growth of control and SHMT1 KO Jurkat xenograft (n=4, bold line representing the average size)
Figure 11B:
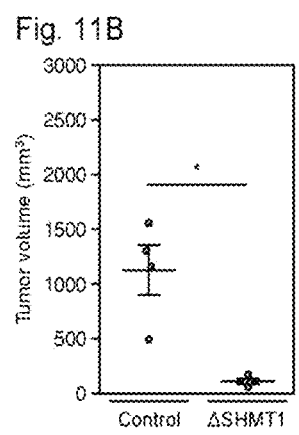
FIG. 11B shows tumors 8 weeks post injection of control (left) and SHMT1 KO (right) Jurkat cells. (n=4, *P<0.05; Mann-Whitney U test)
Figure 11C:
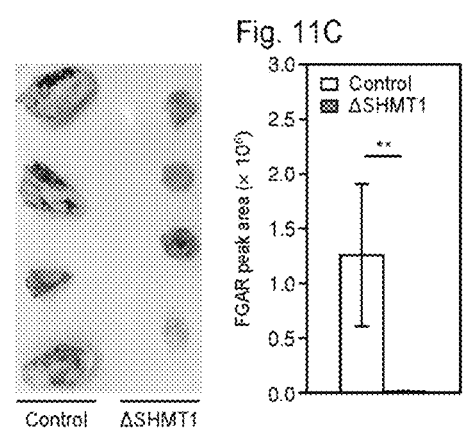
FIG. 11C shows FGAR peak areas in control and SHMT1 KO Jurkat xenografts (n=5, **P<0.01 by two-sample t-test)

To evaluate tumor growth in vivo, SHMT1 control and KO Jurkat cells were implanted onto the hind flanks of immunocompromised NOD/SCID mice. As expected, SHMT1 KO tumors grew significantly slower, resulting in a significant ~5-fold smaller tumor volume after 8 weeks (p-value<0.05; FIGS. 9E and 9F, FIGS. 11A and 11B). Metabolomics analysis of the xenograft tumors showed a similar phenotype found in vitro; TS flux was inhibited in the SHMT1 KO tumors, showing ~100-fold increase in UMP to dTMP ratio compared to the SHMT1 control tumors (p-value<0.01, FIG. 9G). Furthermore, it was find that SHMT1 KO tumors had a major ~15-fold drop in the intratumor 10-formyl-THF pool (p-value<0.05, FIG. 9H), inhibiting purine biosynthesis; as evident by the major accumulation of phosphoribosyl-N-formylglycineamide (FGAR; p-value<0.01; FIG. 11C). Consistently, the concentration of AMP and GMP drop 10- and 6-fold in SHMT1 KO tumors, respectively (p-value<0.01) (FIG. 9H). Overall, these results confirm that cytosolic 1C flux via SHMT1 is essential for purine and pyrimidine biosynthesis in low RFC expressing Jurkat tumors.

TABLE 1

The measured uptake/secretion rates of serine, glycine, and formate of CCRF-CEM in high and physiological media folate levels.

| Media folate | High | Physio. | High | Physio. | High | Physio. |
|---|---|---|---|---|---|---|
| Metabolite | Serine | Serine | Glycine | Glycine | Formate | Formate |
| Mean [mM/h] | 7.74 | 1.68 | −0.08 | 0.84 | −1.24 | −0.18 |
| SD [mM/h] | 0.016 | 0.03 | 0.02 | 0.06 | 0.03 | 0.01 |

TABLE 2

The fractional labeling of intracellular serine, glycine, and dTTP when feeding CCRF-CEM with [2,3,3-$^2$H]-serine for 24 h in high and physiological media folate levels.

| Metabolite | Mass-isotopomer | High folate (mean) | High folate (sd) | Physio. folate (mean) | Physio. folate (sd) |
|---|---|---|---|---|---|
| Serine | M + 0 | 0.07 | 0.007 | 0.08 | 0.008 |
| Serine | M + 1 | 0.01 | 0.001 | 0 | 0 |
| Serine | M + 2 | 0.14 | 0.004 | 0.1 | 0.008 |
| Serine | M + 3 | 0.78 | 0.009 | 0.82 | 0.015 |
| Glycine | M + 0 | 0.23 | 0.058 | 0.6 | 0.05 |
| Glycine | M + 1 | 0.77 | 0.058 | 0.4 | 0.05 |
| dTTP | M + 0 | 0.18 | 0.014 | 0.14 | 0.01 |
| dTTP | M + 1 | 0.65 | 0.028 | 0.24 | 0.01 |
| dTTP | M + 2 | 0.17 | 0.017 | 0.62 | 0.01 |

TABLE 3

The fractional labeling of media serine and glycine when feeding CCU-CEM with [2,3,3-$^2$H]-serine for 24 h in high and physiological media folate levels.

| Metabolite | Mass-isotopomer | High folate (mean) | High folate (sd) | Physio. folate (mean) | Physio. folate (sd) |
|---|---|---|---|---|---|
| Serine | M + 0 | 0.01 | 0 | 0,01 | 0.001 |
| Serine | M + 1 | 0 | 0 | 0 | 0 |
| Serine | M + 2 | 0 | 0.001 | 0 | 0.001 |
| Serine | M + 3 | 0.99 | 0.001 | 0.99 | 0.002 |
| Glycine | M + 0 | 1 | 0 | 1 | 0 |
| Glycine | M + 1 | 0 | 0 | 0 | 0 |

TABLE 4

A compartmentalized network model of 1C metabolism used for MFA.

| Reaction # | Reaction desctiption | Reaction type | Hydrogen mapping |
|---|---|---|---|
| v1 | Serine_Media <=> Serine_CY | Uptake/Secretion | abc => abc |
| v2 | Glucose_Media => Serine_CY | Uptake/Secretion | abc => abc |
| v9 | Glycine_CY <=> Glycine_Media | Uptake/Secretion | a => a |
| v17 | Formate CY => Formate_Media | Uptake/Secretion | a => a |
| v10 | 5,10-meTHF_CY => TMP_CY | Demand | ab => ab |
| v15 | Serine_SY => Serine_Pool | Demand | abc => abc |
| v16 | Glycine_CY => Glycine_Pool | Demand | a => a |
| v18 | 10-formyl-THF_CY => Purines | Demand | a => a |
| v3 | Serine_CY <=> Serine_MT | Others | abc => abc |
| v4 | Serine_MT <=> Glycine_MT + 5,10-meTHF_MT | Others | abc => a + bc |
| v5 | 5,10-meTHF_MT <=> NAD(P)H + 10-formyl-THF_MT | Others | ab => (a + b) or (b + a) |
| v7 | Serine_CY <=> Glycine_CY + 5,10-meTHF_CY | Others | abc => a + bc |
| v8 | Glycine_CY <=> Glycine_MT | Others | a => a |
| v12 | NAD(P)H + 10-formyl-THF_CV <=> 5,10-meTHF_CY | Others | (a + b) or b + a) => ab |
| v19 | Formate_CY <=> 10-formyl-THF_CY | Others | a => a |
| v20 | Formate _MT <=> Formate_CY | Others | a => a |
| v21 | 10-formyl-THF_MT <=> Formate_MT | Others | a => a |

The invention claimed is:

1. A method for treating cancer in an individual comprising:
   a. obtaining a biopsy of the cancer;
   b. measuring one or both of: (i) a level reduced folate carrier (RFC) in cancer cells of the biopsy, and (ii) a level folylpolyglutamate synthetase (FPGS) in cancer cells of the biopsy;
   c. determining one or both of: (i) whether the level of RFC in the cancer cells is above or below a first predetermined threshold value, and (ii) whether the level of FPGS folylpolyglutamate synthetase (FPGS) in the cancer cells is above or below a second predetermined threshold value;
   d. if the level of RFC in the cancer cells is below the first predetermined threshold, treating the individual with an inhibitor of serine-hydroxymethyltransferase (SHMT)1 in a pharmaceutically acceptable carrier;
   e. if the level of FPGS in the cancer cells is below the second predetermined threshold, treating the individual with an inhibitor of serine-hydroxymethyltransferase (SHMT)1 in a pharmaceutically acceptable carrier; and or FPGS
   f. if the level of RFC in the cancer cells is above the first predetermined threshold, treating the individual with an inhibitor of serine-SHMT2 in a pharmaceutically acceptable carrier; and
   g. if the level of FPGS in the cancer cells is above the second predetermined threshold, treating the individual with an inhibitor of serine-SHMT2 in a pharmaceutically acceptable carrier.

2. The method according to claim 1 wherein the inhibitor of SHMT1 has a higher specificity for SHMT1 over SHMT2.

3. The method according to claim 1 wherein the inhibitor of SHMT2 has a higher specificity for SHMT2 over SHMT1.

4. The method according to claim 1 wherein the step of measuring a level of RFC comprises determining an amount of RFC in the cancer cells.

5. The method according to claim 1 wherein the step of measuring a level of RFC comprises measuring an expression level of the gene SLC19A1.

6. The method according to claim 5 wherein the expression level of the gene SLC19A1 is measured in units selected from the list comprising (a) reads per kilobase of transcript per million mapped reads (RPKM), (b) fragments per kilobase of transcript (FPKM) and (c) transcripts per kilobase million (TPM).

7. The method according to claim 5 wherein the expression level of the gene SLC19A1 is measured in RPKM and the predetermined threshold less than or equal to 4.

8. The method according to claim 7 wherein the expression level of the gene SLC19A1 is measured in RPKM and the predetermined threshold less than or equal to 3.

9. The method according to claim 8 wherein the expression level of the gene SLC19A1 is measured in RPKM and the predetermined threshold less than or equal to 2.

10. The method according to claim 1 wherein the SHMT1 inhibitor is a pyrazolopyran derivative.

11. The method according to claim 10 wherein the pyrazolopyran derivative is selected from the list comprising:
   (a) ((4R)-6-amino-4-ethyl-4-(3, 5-chlorophenyl)-1H-pyrano[2,3-c]pyrazole-5-carbonitrile);
   (b) a pyrazolopyran derivative having an isopropyl group at the chiral four-carbon of the pyrano ring; and
   (c) a pyrazolopyran derivative having an aromatic substitution at the chiral four-carbon of the pyrano ring.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
gaacggggcg tatctcatgg                                                    20

<210> SEQ ID NO 2
<211> LENGTH: 27
<212> TYPE: DNA
<213> ORGANISM: Artificial Sequence
<220> FEATURE:
<223> OTHER INFORMATION: Synthetic

<400> SEQUENCE: 2

```
catatttgca tatacgatac aaggctc                                          27
```

<210> SEQ ID NO 3
<211> LENGTH: 58
<212> TYPE: DNA
<213> ORGANISM: Artificial Sequence
<220> FEATURE:
<223> OTHER INFORMATION: Synthetic

<400> SEQUENCE: 3

```
ccggcgacgg tgttcagaat gtgaactcga gttcacattc tgaacaccgt cgttttg       58
```

<210> SEQ ID NO 4
<211> LENGTH: 58
<212> TYPE: DNA
<213> ORGANISM: Artificial Sequence
<220> FEATURE:
<223> OTHER INFORMATION: Synthetic

<400> SEQUENCE: 4

```
ccggccgcaa gcagttccag ttatactcga gtataactgg aactgcttgc ggttttg       58
```

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5

```
cctcgtgtgc tacctttgct t                                                21
```

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6

```
tgatctcgtt cgtgacctgc t                                                21
```

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7

```
ccgagactat ctgcactaca tcc                                              23
```

<210> SEQ ID NO 8
<211> LENGTH: 15
<212> TYPE: DNA
<213> ORGANISM: Artificial Sequence
<220> FEATURE:
<223> OTHER INFORMATION: Synthetic

<400> SEQUENCE: 8

```
gtgccggcag ccttg                                                       15
```

<210> SEQ ID NO 9
<211> LENGTH: 21
<212> TYPE: DNA
<213> ORGANISM: Artificial Sequence

```
<220> FEATURE:
<223> OTHER INFORMATION: Synthetic

<400> SEQUENCE: 9
cacctgcagg aaacaagttt c                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
gtcacaccat cctcacggta g                                              21
```